US007449026B2

(12) United States Patent
Zalesky et al.

(10) Patent No.: US 7,449,026 B2
(45) Date of Patent: Nov. 11, 2008

(54) INTRA-CAVITY CATHETERS AND METHODS OF USE

(75) Inventors: Paul J. Zalesky, Cranston, RI (US); Marc D. Friedman, Needham, MA (US); Stephen Evans, Westford, MA (US)

(73) Assignee: LumeRx, Inc., Newton, MA (US)

( * ) Notice: Subject to any disclaimer, the term of this patent is extended or adjusted under 35 U.S.C. 154(b) by 310 days.

(21) Appl. No.: 10/987,197

(22) Filed: Nov. 12, 2004

(65) Prior Publication Data

US 2005/0131500 A1 Jun. 16, 2005

Related U.S. Application Data

(63) Continuation-in-part of application No. 10/878,648, filed on Jun. 28, 2004, now Pat. No. 7,135,034, and a continuation-in-part of application No. 10/878,649, filed on Jun. 28, 2004, now Pat. No. 7,261,730.

(60) Provisional application No. 60/520,465, filed on Nov. 14, 2003.

(51) Int. Cl.
*A61N 5/06* (2006.01)

(52) U.S. Cl. .............................. 607/88; 607/89; 606/7; 606/15; 128/898

(58) Field of Classification Search .................. 607/88, 607/89; 606/7, 15; 128/898
See application file for complete search history.

(56) References Cited

U.S. PATENT DOCUMENTS

| 4,195,637 | A | | 4/1980 | Gruntzig et al. | |
|---|---|---|---|---|---|
| 4,998,930 | A | | 3/1991 | Lundahl | |
| 5,104,392 | A | * | 4/1992 | Kittrell et al. | 606/15 |
| 5,125,925 | A | | 6/1992 | Lundahl | |
| 5,165,773 | A | | 11/1992 | Nath | |
| 5,342,301 | A | | 8/1994 | Saab | |
| 5,342,305 | A | | 8/1994 | Shonk | |
| 5,344,419 | A | | 9/1994 | Spears | |
| 5,354,293 | A | | 10/1994 | Beyer et al. | |
| 5,415,654 | A | | 5/1995 | Daikuzono | |
| 5,440,461 | A | | 8/1995 | Nadel et al. | |
| 5,445,608 | A | * | 8/1995 | Chen et al. | 604/20 |

(Continued)

FOREIGN PATENT DOCUMENTS

WO      WO 98/32493       7/1998

(Continued)

OTHER PUBLICATIONS

International Search Report for PCT/US2006/019522, Oct. 30, 2006.

*Primary Examiner*—Ahmed M Farah
(74) *Attorney, Agent, or Firm*—Dana M. Gordon; Foley Hoag LLP

(57) ABSTRACT

Catheters for performing therapeutic and diagnostic procedures within a body, including human or animal body cavities or lumens, and methods for use. One or more distancing member of the catheter can be used to position a sensor or a therapeutic device a minimum distance from a wall of a lumen or cavity. The catheter can include means for actively or passively controlling or modulating its position within the lumen or cavity during a procedure. Methods for using the catheter include nonocclusive deployment in the human gastrointestinal tract for phototherapy procedures, delivering electromagnetic radiation substantially homogeneously or in a desired pattern to the interior of a lumen.

15 Claims, 21 Drawing Sheets

U.S. PATENT DOCUMENTS

| | | | |
|---|---|---|---|
| 5,452,182 A | 9/1995 | Eichelberger et al. | |
| 5,458,575 A | 10/1995 | Wang | |
| 5,514,091 A | 5/1996 | Yoon | |
| 5,514,669 A | 5/1996 | Selman | |
| 5,519,596 A | 5/1996 | Woolverton | |
| 5,558,668 A | 9/1996 | Lankford et al. | |
| 5,607,419 A | 3/1997 | Amplatz et al. | |
| 5,720,717 A | 2/1998 | D'Andrea | |
| 5,725,521 A * | 3/1998 | Mueller | 606/7 |
| 5,766,234 A | 6/1998 | Chen et al. | |
| 5,788,708 A | 8/1998 | Hegde et al. | |
| 5,800,478 A | 9/1998 | Chen et al. | |
| 5,814,039 A | 9/1998 | Prescott | |
| 5,861,020 A | 1/1999 | Schwarzmaier | |
| 5,876,426 A | 3/1999 | Kume et al. | |
| 5,876,427 A | 3/1999 | Chen et al. | |
| 5,947,924 A | 9/1999 | Liprie | |
| 5,957,960 A | 9/1999 | Chen et al. | |
| 5,997,569 A | 12/1999 | Chen et al. | |
| 5,997,571 A | 12/1999 | Farr et al. | |
| 6,013,053 A | 1/2000 | Bower et al. | |
| 6,086,558 A | 7/2000 | Bower et al. | |
| 6,146,409 A | 11/2000 | Overholt et al. | |
| 6,159,236 A | 12/2000 | Biel | |
| 6,187,014 B1 | 2/2001 | Goodin et al. | |
| 6,224,590 B1 | 5/2001 | Daikuzono | |
| 6,254,570 B1 | 7/2001 | Rutner et al. | |
| 6,267,717 B1 | 7/2001 | Stoll | |
| 6,290,713 B1 | 9/2001 | Russell | |
| 6,364,874 B1 | 4/2002 | Bays et al. | |
| 6,371,637 B1 | 4/2002 | Atchinson et al. | |
| 6,443,978 B1 | 9/2002 | Zharov | |
| 6,480,389 B1 | 11/2002 | Shie et al. | |
| 6,491,618 B1 | 12/2002 | Ganz | |
| 6,491,662 B1 | 12/2002 | Liprie et al. | |
| 6,491,672 B2 | 12/2002 | Slepian et al. | |
| 6,514,192 B2 | 2/2003 | Tiren | |
| 6,566,824 B2 | 5/2003 | Panagotacos et al. | |
| 6,580,228 B1 | 6/2003 | Chen et al. | |
| 6,605,084 B2 | 8/2003 | Acker et al. | |
| 6,610,083 B2 | 8/2003 | Keller et al. | |
| 6,626,900 B1 | 9/2003 | Sinofsky et al. | 606/15 |
| 6,645,230 B2 | 11/2003 | Whitehurst | |
| 6,682,525 B2 | 1/2004 | Lalonde et al. | |
| 6,699,170 B1 | 3/2004 | Crocker et al. | |
| 6,702,782 B2 | 3/2004 | Miller et al. | |
| 6,706,004 B2 | 3/2004 | Tearney et al. | |
| 6,706,010 B1 | 3/2004 | Miki et al. | |
| 6,712,074 B2 * | 3/2004 | Edwards et al. | 128/898 |
| 6,712,833 B1 | 3/2004 | Lee et al. | |
| 6,719,720 B1 | 4/2004 | Voelker et al. | |
| 6,723,053 B2 | 4/2004 | Ackerman et al. | |
| 6,723,070 B1 | 4/2004 | Arai et al. | |
| 6,723,113 B1 | 4/2004 | Shkolnik | |
| 6,733,487 B2 | 5/2004 | Keith et al. | |
| 6,733,512 B2 | 5/2004 | McGhan | |
| 6,736,808 B1 | 5/2004 | Motamedi et al. | |
| 6,736,827 B1 | 5/2004 | McAndrew et al. | |
| 6,740,104 B1 | 5/2004 | Solar et al. | |
| 6,743,227 B2 | 6/2004 | Seraj et al. | |
| 6,746,423 B1 | 6/2004 | Wantink | |
| 6,746,424 B2 | 6/2004 | Stamberg | |
| 6,749,583 B2 | 6/2004 | Briscoe et al. | |
| 6,749,623 B1 | 6/2004 | Hsi et al. | |
| 6,815,724 B2 | 11/2004 | Dry | |
| 6,831,303 B2 | 12/2004 | Dry | |
| 6,962,584 B1 * | 11/2005 | Stone et al. | 606/7 |
| 6,984,229 B2 * | 1/2006 | Neuberger | 606/15 |
| 7,165,551 B2 * | 1/2007 | Edwards et al. | 128/898 |
| 2001/0049464 A1 | 12/2001 | Ganz | |
| 2001/0053920 A1 | 12/2001 | Shaker | |
| 2002/0010500 A1 | 1/2002 | Chen | |
| 2002/0055748 A1 | 5/2002 | Gellman et al. | |
| 2002/0135665 A1 | 9/2002 | Gardner | |
| 2002/0165521 A1 | 11/2002 | Cioanta et al. | |
| 2002/0183620 A1 | 12/2002 | Cioanta et al. | |
| 2003/0028182 A1 | 2/2003 | Abboud et al. | |
| 2003/0032950 A1 | 2/2003 | Altshuler et al. | |
| 2003/0090893 A1 | 5/2003 | Nepil | |
| 2003/0123225 A1 | 7/2003 | Miller | |
| 2003/0191459 A1 | 10/2003 | Ganz et al. | |
| 2003/0201542 A1 | 10/2003 | Wu | |
| 2004/0037080 A1 | 2/2004 | Luk et al. | |
| 2004/0039242 A1 | 2/2004 | Tolkoff et al. | |
| 2004/0059397 A1 | 3/2004 | Sinofsky et al. | 607/88 |
| 2004/0093044 A1 | 5/2004 | Rychnovsky et al. | |
| 2004/0223328 A1 | 11/2004 | Lee et al. | |
| 2004/0225322 A1 | 11/2004 | Garrison et al. | |
| 2005/0030765 A1 | 2/2005 | Southard et al. | |

FOREIGN PATENT DOCUMENTS

| | | |
|---|---|---|
| WO | WO 98/43703 | 10/1998 |
| WO | WO 2004/082736 | 9/2004 |
| WO | WO 2005/058407 | 6/2005 |
| WO | WO2005/004704 A2 | 10/2005 |

* cited by examiner

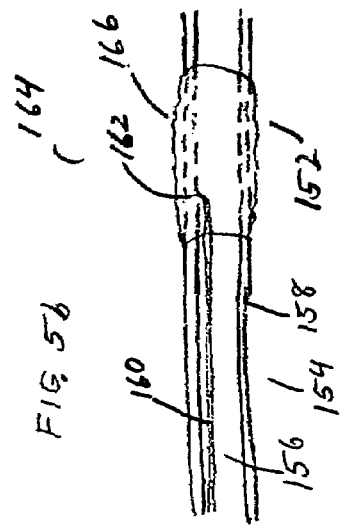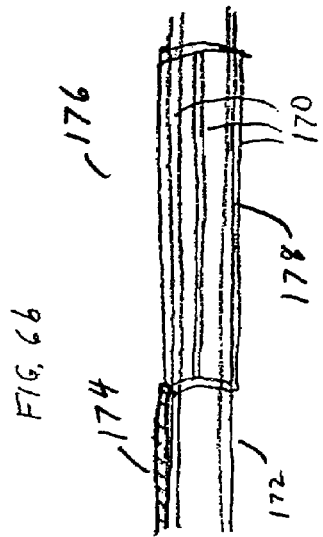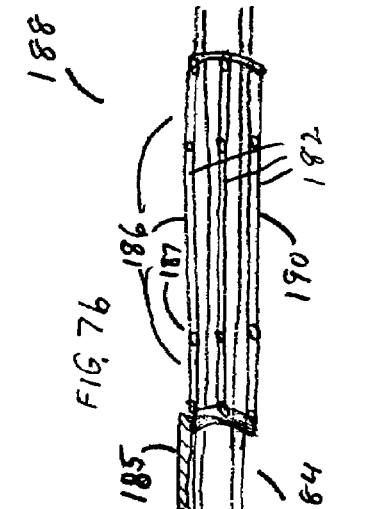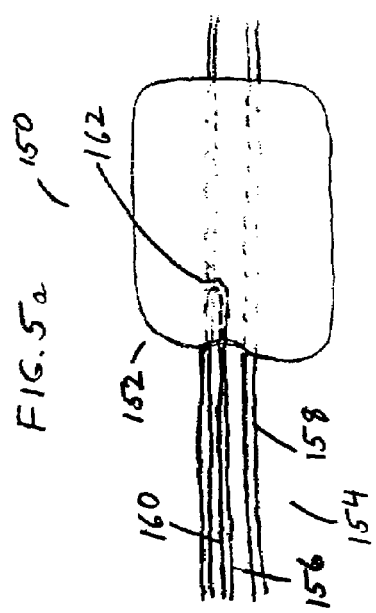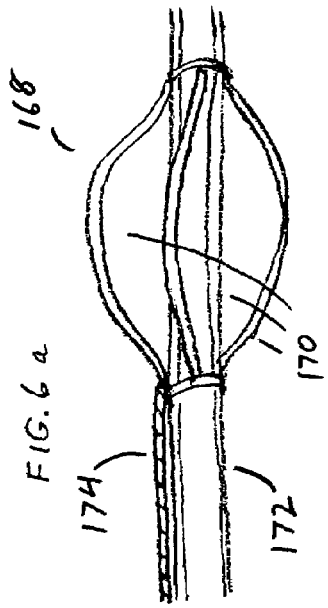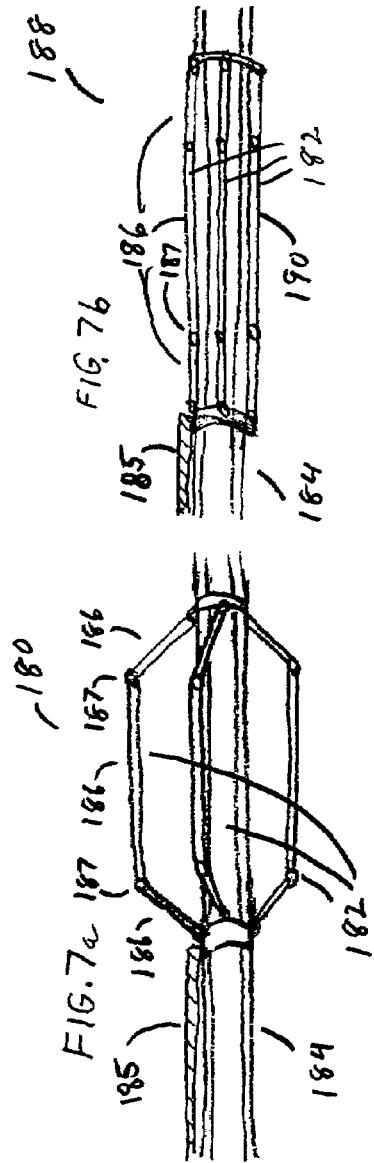

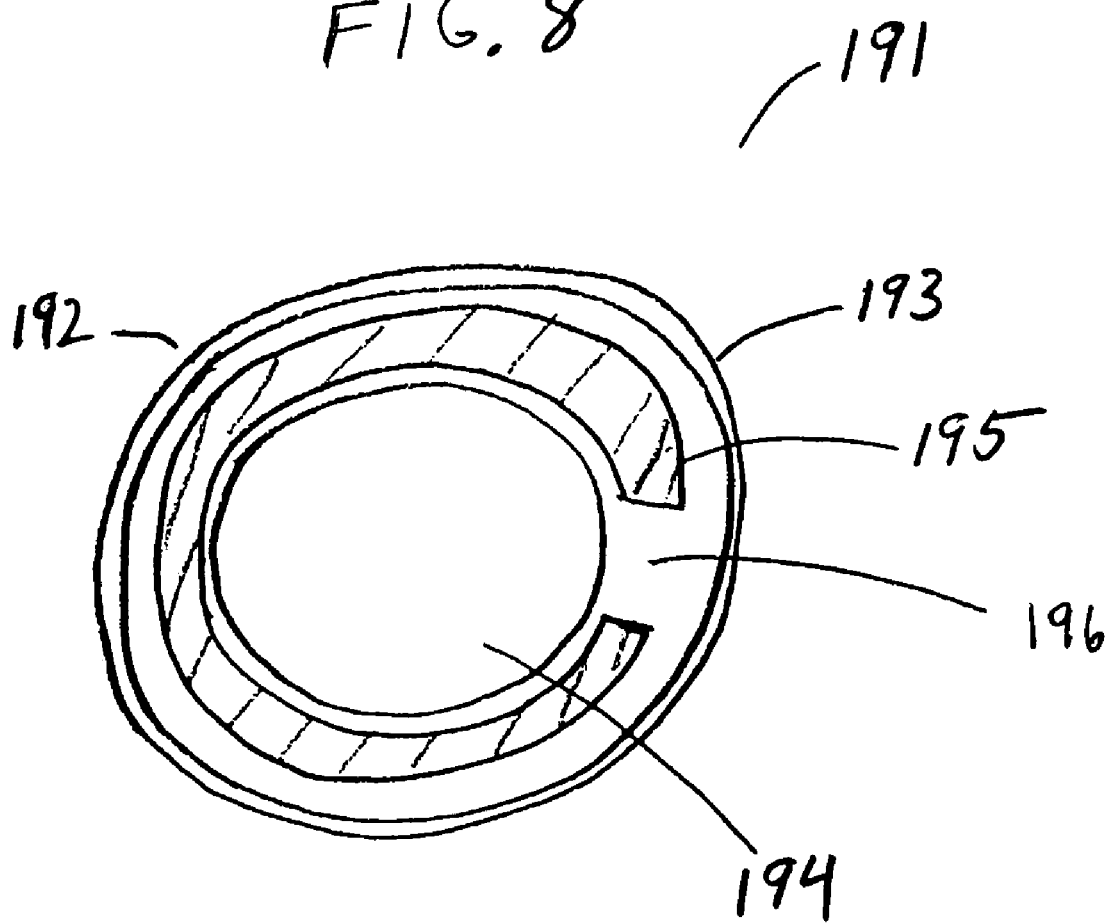

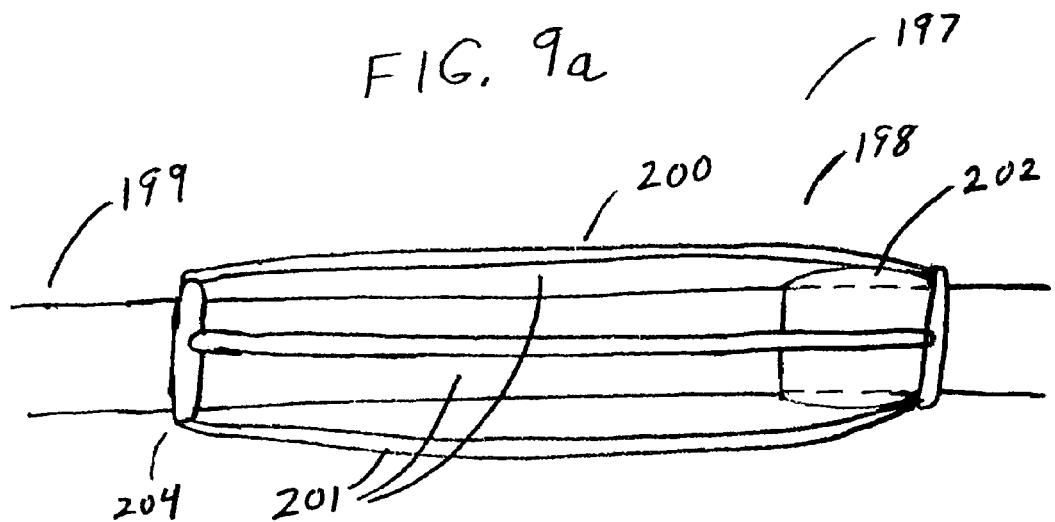
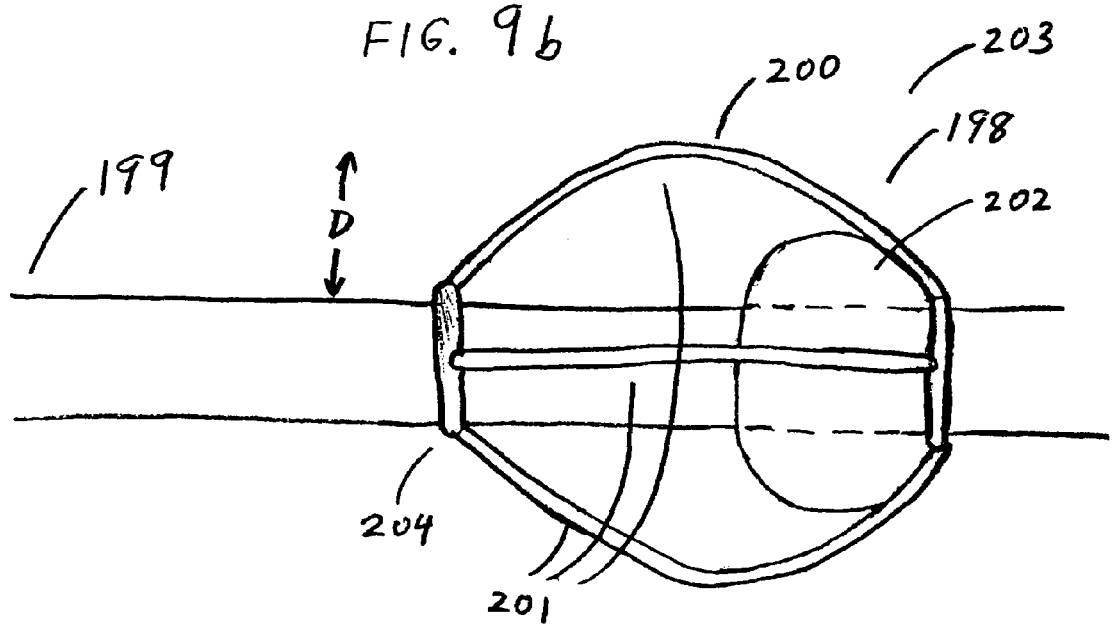

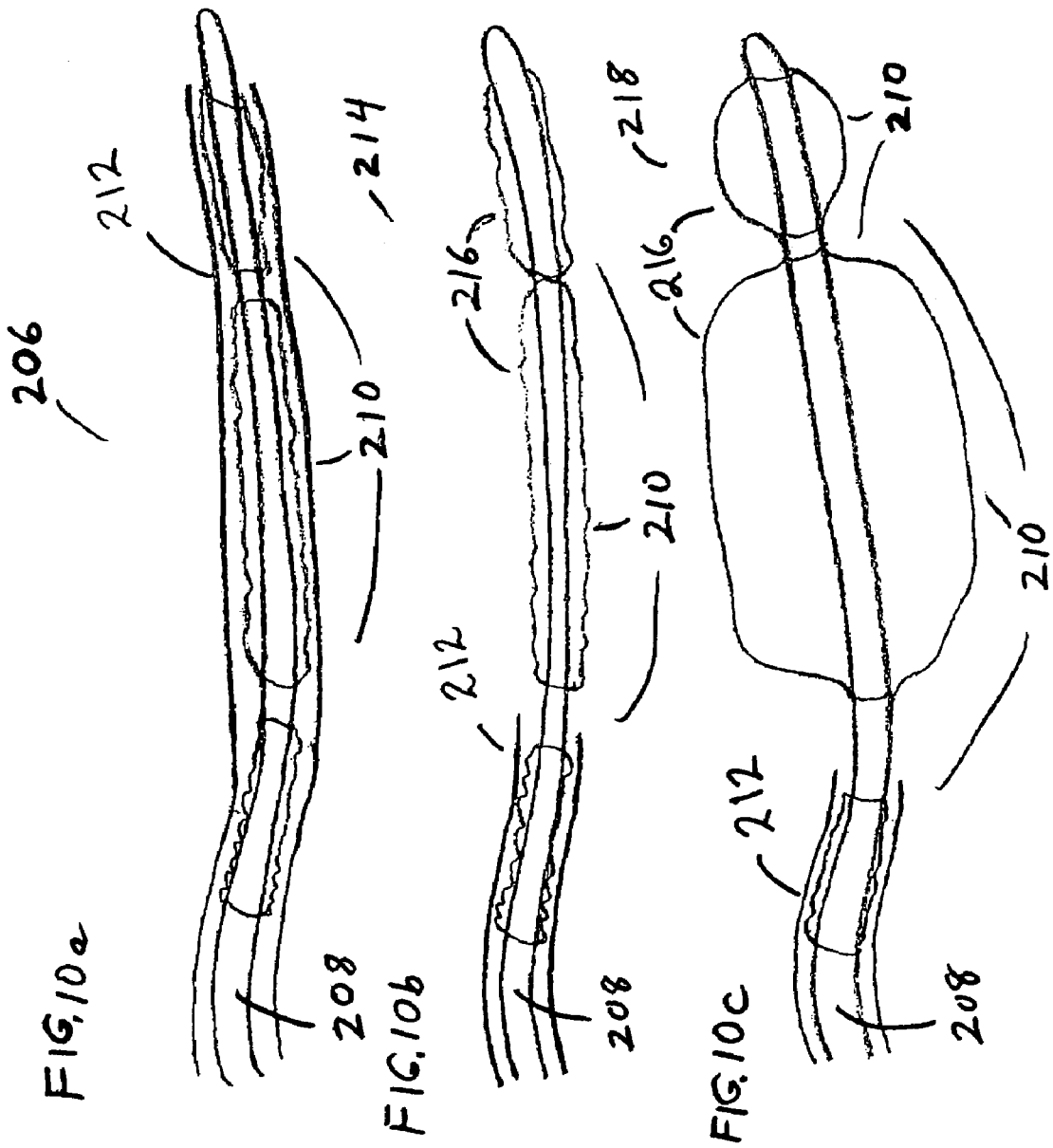

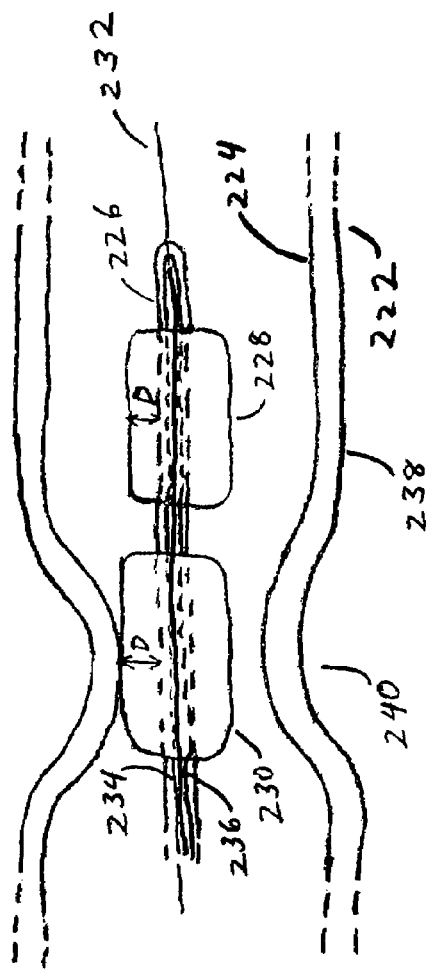
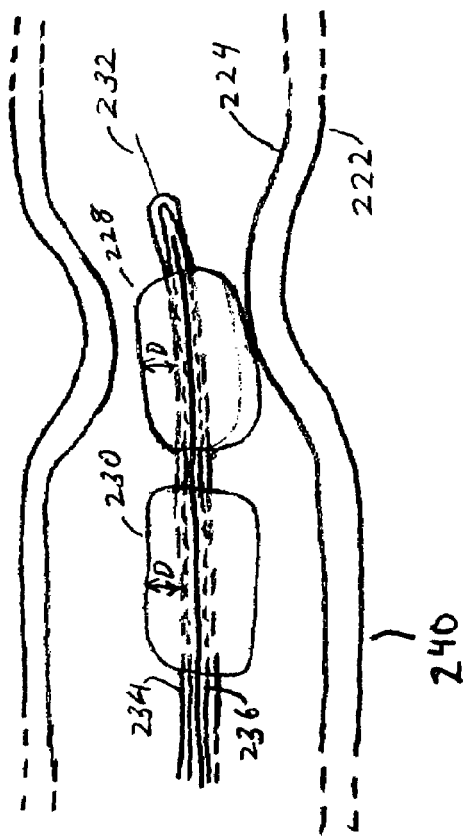
FIG. 11a
FIG. 11b

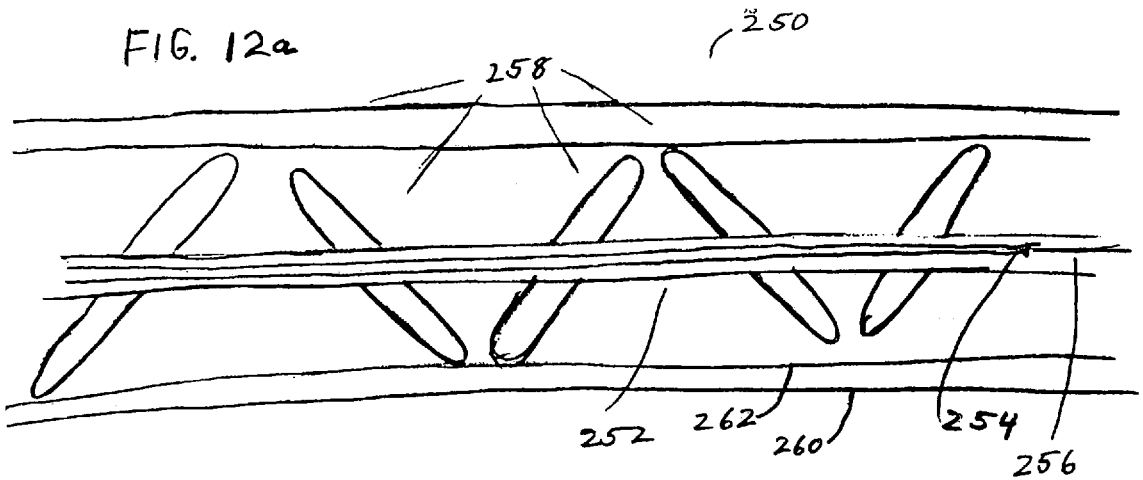
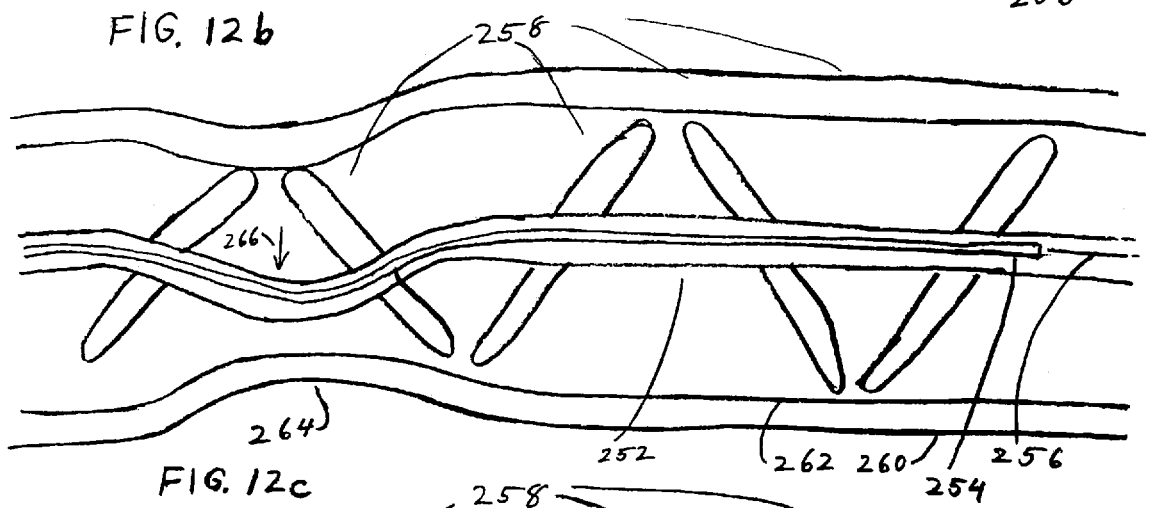
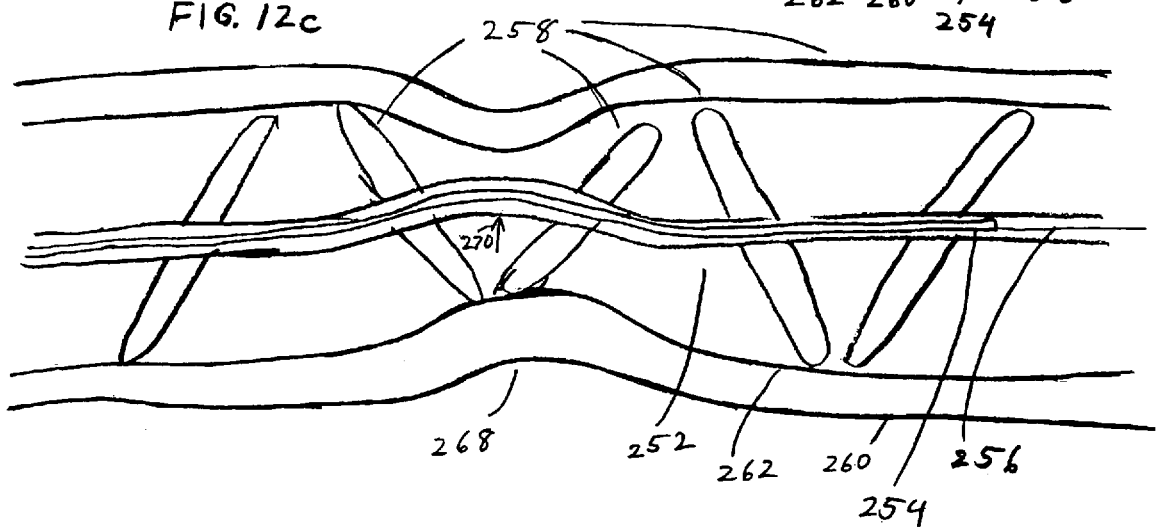

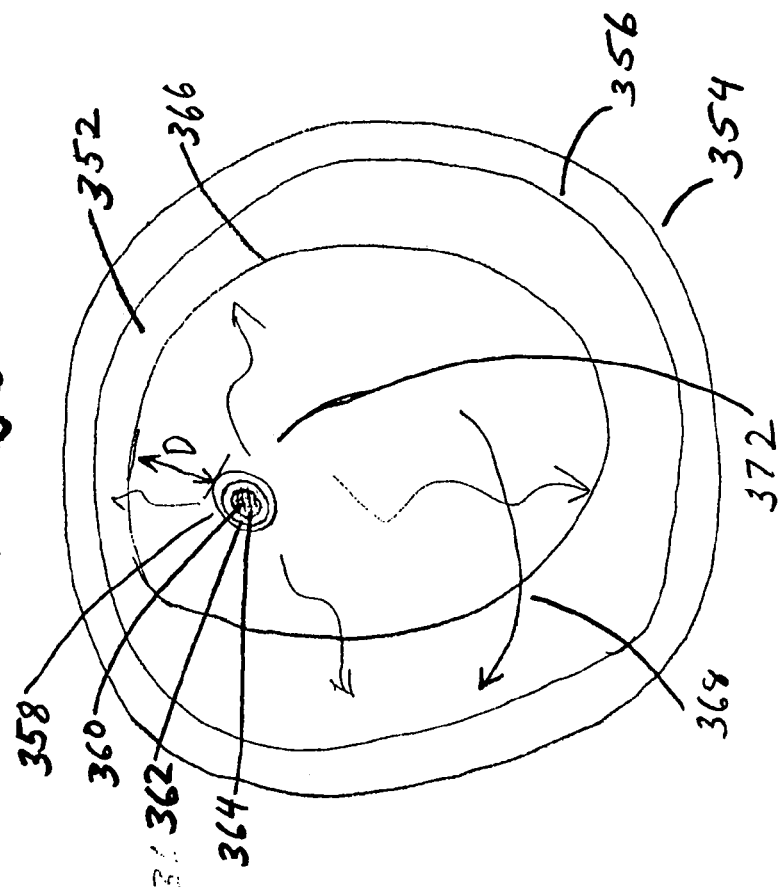
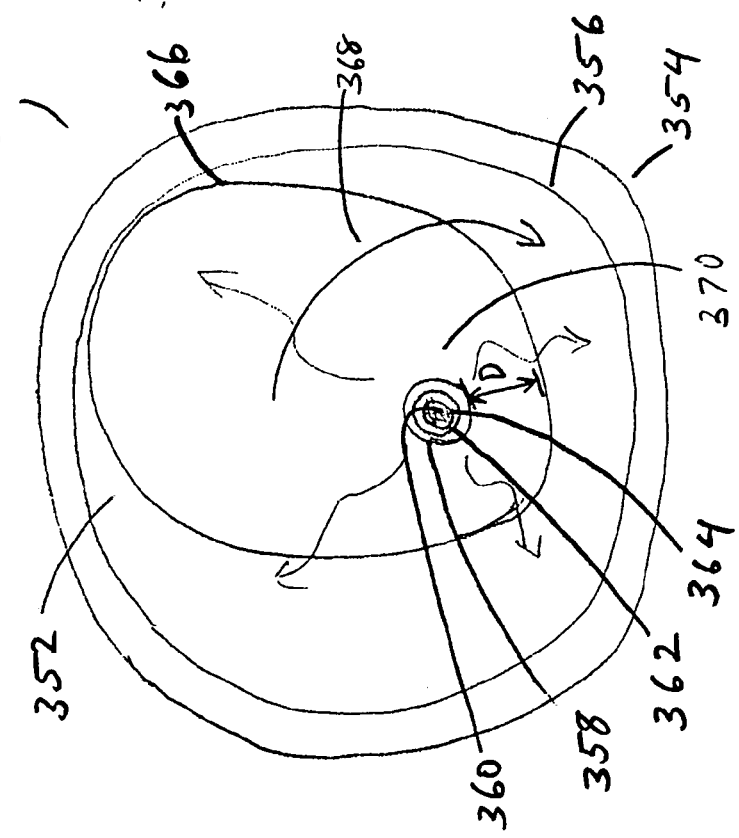

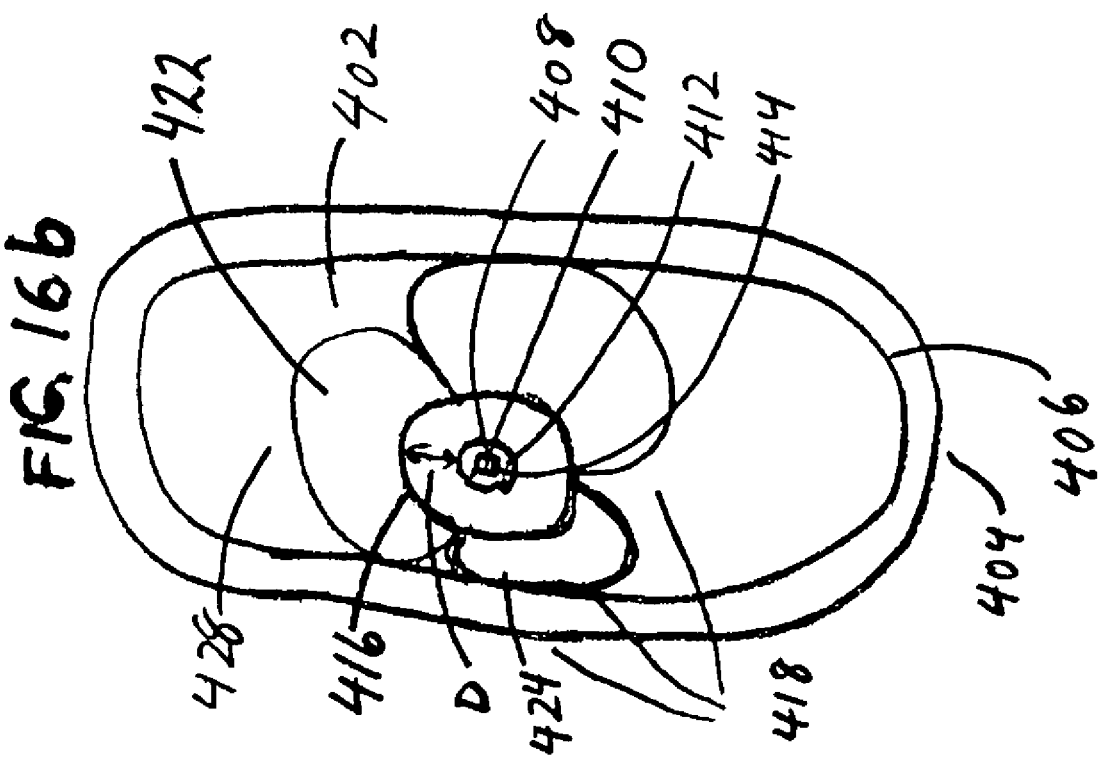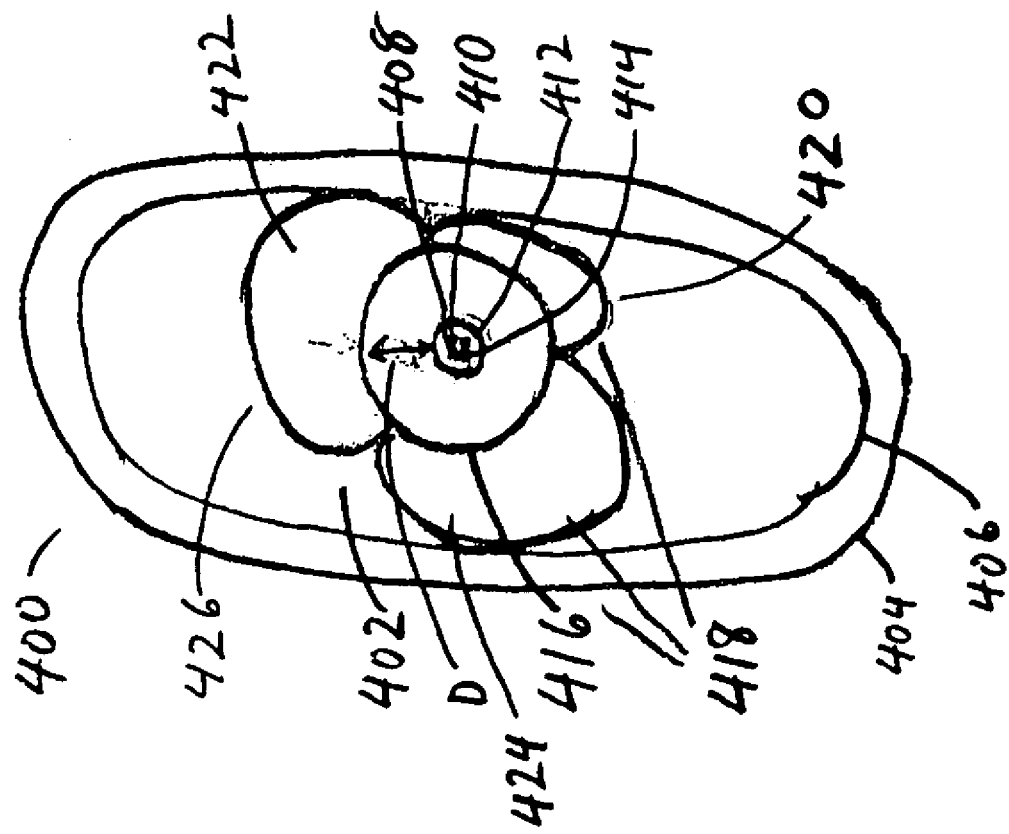

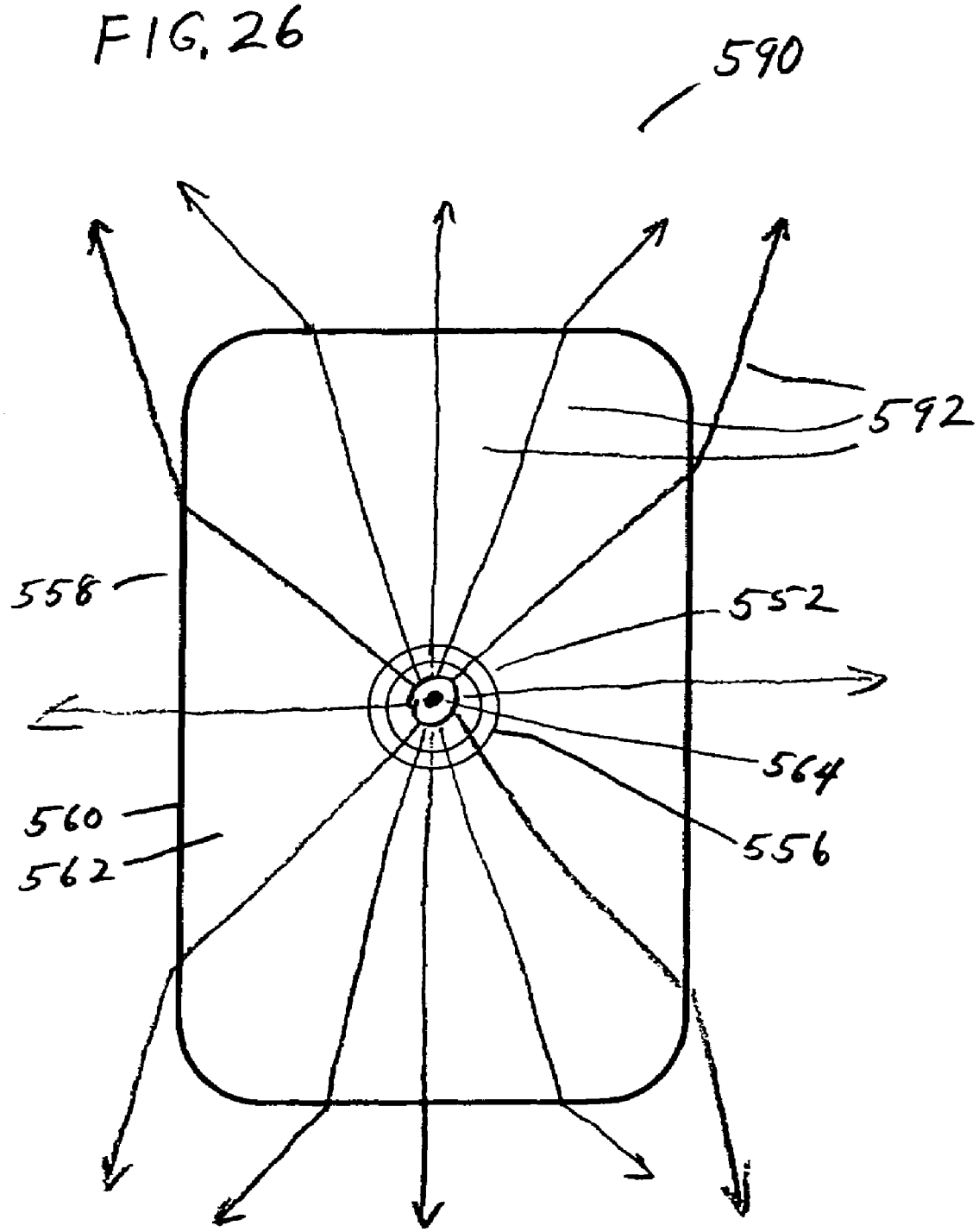

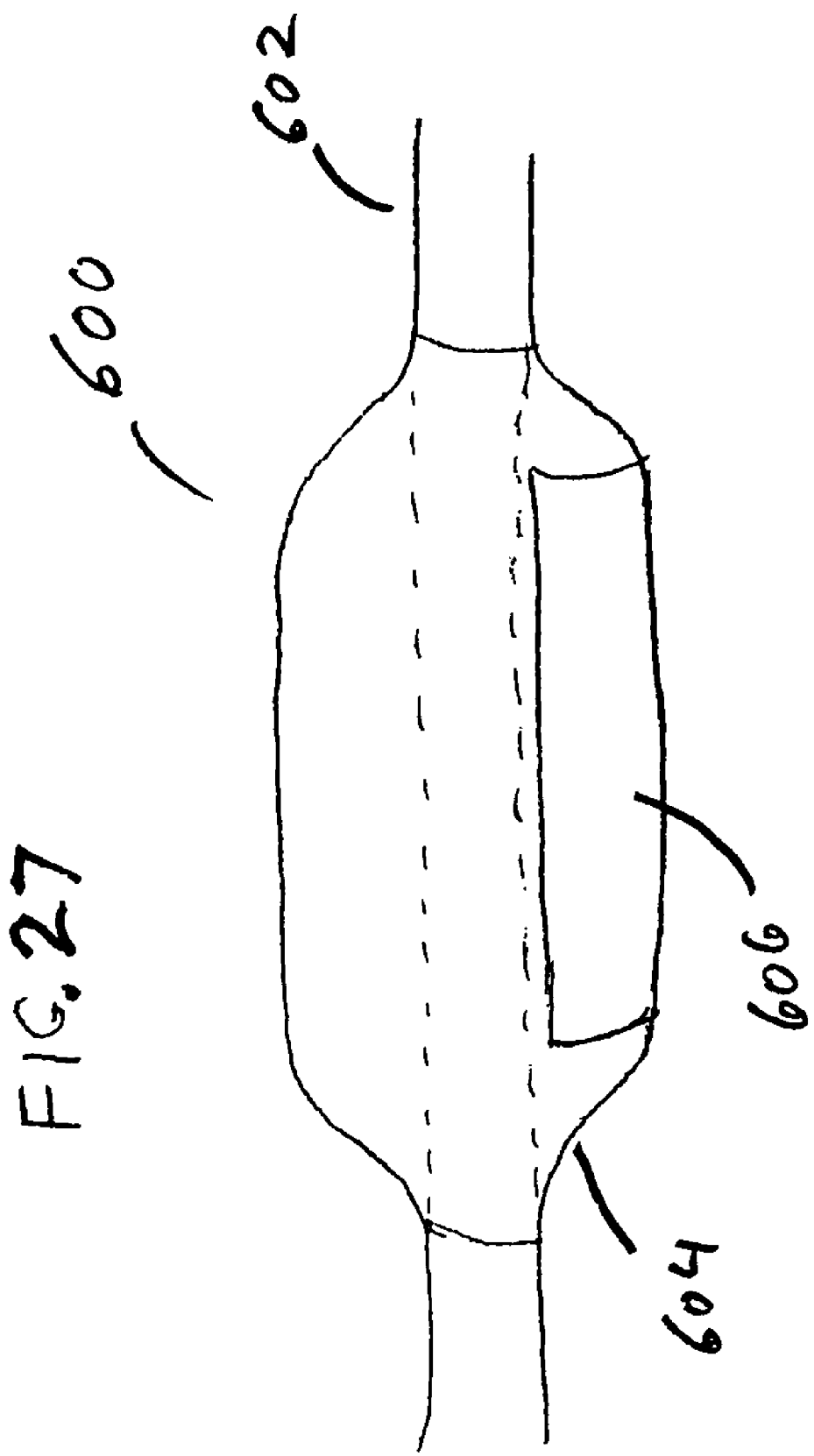

US 7,449,026 B2

INTRA-CAVITY CATHETERS AND METHODS OF USE

RELATED APPLICATIONS

This application incorporates by reference, and claims priority to and the benefit of U.S. Provisional Patent Application No. 60/520,465, filed on Nov. 14, 2003; U.S. patent application Ser. No. 10/878,648, filed on Jun. 28, 2004; and U.S. patent application Ser. No. 10/878,649 filed on Jun. 28, 2004.

FIELD

Disclosed herein are methods and apparatus associated with catheters for the delivery of medical devices to, and performance of procedures in the interior of lumens or cavities and, more particularly, to methods and apparatus for phototherapy.

BACKGROUND

The construction and use of medical catheters is well known in the art. Balloons or other expansion devices are sometimes incorporated with catheters for such purposes as dilating blood vessels or other hollow structures (lumens) within a body, for temporarily anchoring an instrument within the body so that a surgical procedure can be performed, for cryotherapy and for phototherapy. Catheters including one or more balloons have been used to securely position light-emitters within a lumen such as in the human gastrointestinal tract, typically targeting a specific treatment area on a wall of the lumen to destroy malignant tumor cells that have preferentially retained a photosensitizing drug, while avoiding the irradiation of adjacent normal tissue.

Expandable catheters such as balloon catheters known in the art are generally occlusive devices that when expanded either conform to the interior shape of a lumen (sometimes referred to as being distensible balloon catheters), or force the lumen to expand to accommodate the size and shape of the balloon (sometimes referred to as being non-distensible balloon catheters). These devices are useful for such procedures as angioplasty, where a significant outward radial force is needed to expand an occluded blood vessel, or for situations where the exact placement of a medical instrument within a lumen is critical and requires complete immobilization of the lumen, for example, when a directed dose of radiation must be delivered to a specific surface segment of the lumen without irradiating adjacent surfaces.

Medical procedures using devices that immobilize or distend a lumen can put a patient at risk by blocking fluid flow, by abrading tissue, or by applying damaging force to the lumen or connected structures. Such devices also may not optimally present the interior surface of the lumen for uniform access during a medical procedure. In addition, some lumens have highly asymmetric or irregular shapes that are at best awkwardly addressed by existing balloon catheters and associated methods of use.

Thus, a significant need exists for improved procedures using expandable catheters and for new catheters that overcome the shortcomings associated with present devices.

SUMMARY

Disclosed herein are methods, devices and systems for performing medical procedures in the interior of a lumen, including the delivery of electromagnetic radiation such as light to the interior of the lumen. The term lumen is used herein to mean the interior of a hollow organ in a human or animal body, and more generally, to refer to any tubular or hollow item or cavity. Among other things, embodiments disclosed herein also relate to methods and systems for the diagnosis and treatment of infections within a lumen, methods and systems for phototherapy, both with and without photosensitizers, and methods and systems for treatment of cancers and precancerous conditions.

One exemplary embodiment is a method for delivering radiation to a cavity that has an interior surface. The cavity may be a lumen. In one embodiment, the method includes positioning a catheter in the cavity. The catheter includes a radiation source, an insufflation device and at least one distancing member that can be deployed to provide a minimum distance between the radiation source and the interior surface of the cavity while allowing movement of the catheter within the cavity. The radiation source may, in various embodiments, include a light emitting diode, an optical fiber optically coupled to a radiation source located outside the cavity, or another type of radiation source.

The at least one distancing member may be any kind of distancing member, and may include portions that transmit, reflect, or scatter light. In one embodiment, the at least one distancing member includes a balloon that is expandable to provide the minimum distance. In another embodiment, the at least one distancing member includes one or more flexible member that can be flexed to deploy the distancing member. In yet another embodiment, the at least one distancing member includes at least one jointed arm having at least two segments connected by a hinge that is flexed when the distancing member is deployed. The flexing of the flexible member or the flexing of the hinge may be activated by inflating a balloon. In an embodiment, variable deployment of a distancing member may be used to achieve different minimum distances.

The method includes insufflating the cavity using the insufflation device, deploying the at least one distancing member, and delivering radiation to the interior surface of the cavity while allowing movement of the catheter within the cavity. Movement of the catheter within the body may be in response to natural movement of the cavity, or may be actively controlled from outside the cavity. In embodiments, the method is used to treat an infection that may be a *Helicobacter pylori* infection, or to perform a diagnostic procedure.

Another exemplary embodiment is an apparatus for delivering radiation to the interior surface of a cavity. An embodiment of the apparatus includes a catheter, a radiation source positioned within the catheter, an insufflation device capable of expanding the cavity when the catheter is positioned in the cavity, and at least one distancing member coupled to the catheter, the at least one distancing member adapted to establish a minimum distance between the radiation source and the interior surface of the cavity, and to permit the catheter to move within the cavity. The at least one distancing member may have a deployed state and an undeployed state, and in an embodiment, includes at least one balloon that may be deployed by expanding the balloon. The balloon may be made from a material including polyurethane or polyethylene terephthalate. In another embodiment, the at least one distancing member includes at least one flexible member that may be deployed by flexion. The flexion may be activated by inflating a balloon.

In a further embodiment, the apparatus includes a sensor for measuring a distance between the radiation source and the interior surface of the cavity. The radiation source may include a light-emitting diode. The radiation source may also include an optical fiber optically coupled to a radiation source located outside the cavity. In an embodiment, the radiation source emits radiation within a range of wavelengths capable of treating an infection. In an embodiment, the infection is a *Helicobacter Pylori* infection.

Yet another exemplary embodiment is a method for performing a medical procedure on the interior surface of a cavity that may be a lumen. An embodiment of the method includes introducing an elongated member that may be a catheter into the cavity, insufflating the cavity with a fluid, positioning the elongated member a minimum distance from the interior surface of the cavity, moving the elongated member while maintaining the minimum distance, and performing the medical procedure while moving the elongated member within the cavity. In an embodiment, the medical procedure includes illuminating the interior of the lumen. In an embodiment, illuminating the interior of the lumen treats an infection.

Still another exemplary embodiment is an apparatus for delivering radiation to an interior surface of a lumen. An embodiment of the apparatus includes an elongated member, a radiation source positioned within the elongated member, and means for maintaining a minimum distance between the radiation source and the interior surface of the lumen while allowing movement of the elongated member within the lumen when the lumen is insufflated. The apparatus may also include an insufflation device connected to the elongated member.

Yet another exemplary embodiment is a method for delivering radiation to an interior surface of a cavity that may be a lumen. An embodiment of the method includes positioning an elongated member that includes a radiation source within the cavity. The method also includes maintaining a minimum distance between the radiation source and the interior surface of the cavity while allowing movement of the elongated member within the cavity when the cavity is insufflated, and delivering radiation to the interior surface of the lumen using the radiation source.

Yet another exemplary embodiment is a method for positioning an elongated member that includes at least one distancing member, in a body having an interior surface. The body may be a lumen. An embodiment of the method includes introducing the elongated member into the body and deploying the at least one distancing member to provide a minimum distance between the elongated member and the interior surface while allowing movement of the elongated member within the body. In an embodiment, the elongated member is a catheter that may include a light source. In an embodiment, the method includes delivering light to the interior surface. In a further embodiment, the method includes pressurizing the body. In yet another embodiment, the elongated member has a longitudinal axis and the distancing member is adapted to allow movement of the elongated member in a direction transverse to the axis.

BRIEF DESCRIPTION OF THE DRAWINGS

Aspects, features and embodiments of the present invention may be better understood by referring to the following description in conjunction with the accompanying drawings and claims, in which like numerals indicate like structural elements and features in various figures. The drawings are not necessarily to scale, emphasis instead being placed upon illustrating embodiments and features of the invention. These depicted embodiments are to be understood as illustrative of the invention and not as limiting in any way.

FIG. 5a and FIG. 5b illustrate an embodiment of a distancing member of a catheter of the present invention comprising a balloon.

FIG. 6a and FIG. 6b illustrate an embodiment of a distancing member of a catheter of the present invention comprising a plurality of flexible members.

FIG. 7a and FIG. 7b illustrate an embodiment of a distancing member of a catheter of the present invention comprising a plurality of jointed arms.

FIG. 8 illustrates an embodiment of a catheter of the present invention including a catheter body having a longitudinal passage defined by c-cut tubing.

FIG. 9a and FIG. 9b illustrate an embodiment of a distancing member wherein external flexible members are deployed by inflation of a balloon.

FIG. 10a through FIG. 10c illustrate an embodiment of a catheter of the present invention having an insertion sheath.

FIG. 11a and FIG. 11b illustrate an embodiment of a catheter of the present invention deployed in a lumen experiencing peristalsis.

FIG. 12a through FIG. 12c illustrate an embodiment of a catheter of the present invention including distancing members that respond to natural motion of a lumen to modulate the position of a light-emitting device within the lumen.

FIG. 15a and FIG. 15b illustrate an embodiment of a catheter and procedure of the present invention wherein an eccentric distancing member is used for modulating the position of a catheter within a lumen.

FIG. 16a and FIG. 16b illustrate an embodiment of a catheter of the present invention having a plurality of variably deployable distancing members for positioning within a lumen.

FIG. 26 illustrates an embodiment of a catheter of the present invention including a liquid-filled distancing member comprising a balloon for phototherapy.

FIG. 27 illustrates an embodiment of a windowed catheter of the present invention for phototherapy.

DESCRIPTION

Figure 1:
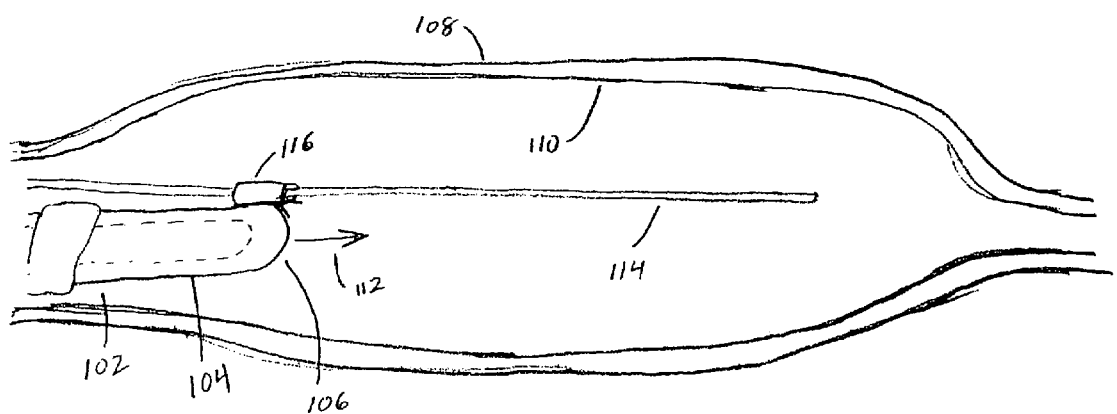
FIG. 1 shows an embodiment of a catheter of the present invention being inserted into a lumen.

Certain exemplary embodiments will now be described to provide an overall understanding of the aspects and features of the methods, apparatus, and systems of use disclosed herein. Examples of these embodiments and features are illustrated in the drawings. Those of ordinary skill in the art will understand that the apparatus, systems and methods of use disclosed herein can be adapted and modified to provide apparatus, systems and methods for other applications and that other additions and modifications can be made without departing from the scope of the present disclosure. For example, the features illustrated or described as part of one embodiment or one drawing can be used on another embodiment or another drawing to yield yet another embodiment. Such modifications and variations are intended to be included within the scope of the present disclosure.

An exemplary embodiment of a method and apparatus for delivering radiation to the interior of a lumen in a medical procedure according to the present invention is illustrated in FIG. 1 through FIG. 4. In this embodiment, the radiation includes electromagnetic radiation. Electromagnetic radiation may be of any wavelength or range of wavelengths, preferably those most effective for carrying out the procedure. In an embodiment, the radiation is visible light. In other embodiments, the radiation may have wavelengths in the infrared, ultraviolet, or x-ray spectral regions. FIG. 1 illustrates an insertion step 100 wherein an elongated member, which in FIG. 1 is a catheter 102 having a flexible catheter body 104 and a distal end 106, is shown being introduced distally into a lumen 108 having a lumen wall 110. In an embodiment, the lumen 108 is an organ of the human digestive tract. In an embodiment, the organ is a stomach. The distal direction of motion of the catheter being introduced into the lumen is indicated in the figure by arrow 112. The catheter 102 may be passed into the lumen 108 from outside the body of a patient using any medical technique appropriate for introducing an elongated object into a lumen. In an embodiment, introducing the catheter 102 into the lumen 108 comprises passing the catheter into the body through a body orifice. In an embodiment, the body orifice is the mouth. In another embodiment, the body orifice is the nose. In another embodiment, the catheter may be delivered to the interior of the lumen 108 through a biopsy channel in an endoscope.

In an embodiment, the catheter 102 is passed into the lumen 108 over a guidewire 114. In a further embodiment, the guidewire 114 is placed in the lumen during a diagnostic endoscopy procedure that precedes the procedure for delivering light to the lumen. In the embodiment shown in FIG. 1 through FIG. 4, the catheter 102 is passed over the guidewire 114 into the lumen using a monorail mechanism 116. In an embodiment, the monorail system 116 comprises a short length of tubing connected to the catheter body 104 near the distal end 106. In another embodiment, the monorail mechanism comprises an eyelet.

Figure 2:
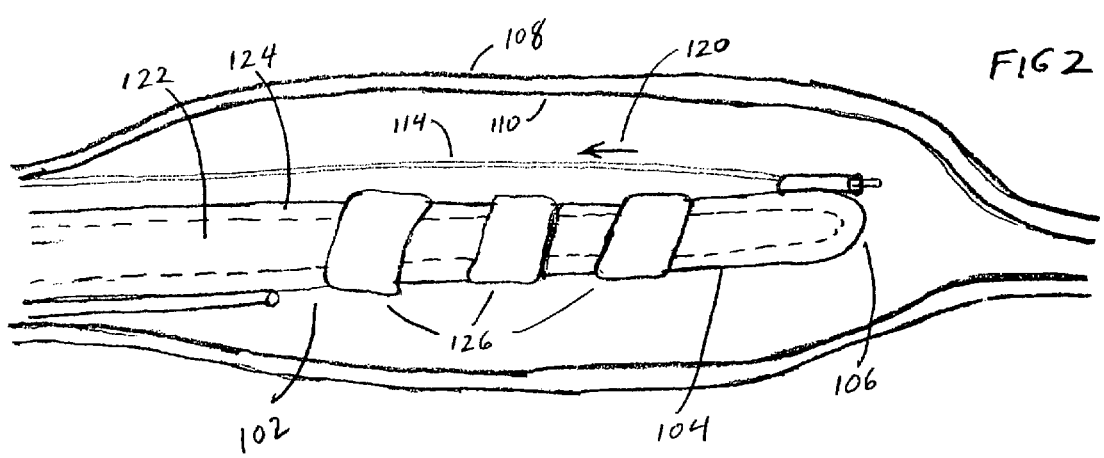
FIG. 2 shows the catheter of FIG. 1 fully inserted into the lumen.

FIG. 2 illustrates a guidewire removal step 118 wherein the catheter 102 is fully introduced into the lumen 108. In an embodiment, the guidewire 114 is removed from the lumen after the catheter 102 is fully introduced into the lumen 108, the direction of removal shown in FIG. 2 by arrow 120. The catheter body 104 includes at least one catheter wall 124, which defines at least one internal longitudinal passage 122. In an embodiment, a portion of the catheter wall 124 is substantially optically transparent to phototherapeutic radiation. In another embodiment, a portion of the catheter wall 124 is substantially optically reflective. In yet another embodiment, a portion of the catheter wall 124 substantially scatters light. In still another embodiment, the catheter wall 124 is patterned with respect to its optical properties.

In an embodiment, the at least one internal longitudinal passage 122 is closed at the distal end 106. In another embodiment, one of the at least one internal longitudinal passage 122 is open at the distal end 106. In a further embodiment, the at least one longitudinal passage 122 open at the distal end 106 is adapted for passing a guidewire 114 entirely longitudinally through the catheter body 104 for introducing the catheter 102 into the lumen 108. The catheter 102 includes one or more distancing members 126. The one or more distancing members 126 can be reversibly deployed from an undeployed position close to the catheter body 104. In an embodiment, the one or more distancing members 126 substantially circumferentially surround a longitudinal portion of the catheter body 104. FIG. 2 illustrates the one or more distancing members 126 undeployed, providing a minimum effective cross sectional area of the catheter 102 for insertion into the lumen 108.

Figure 3:
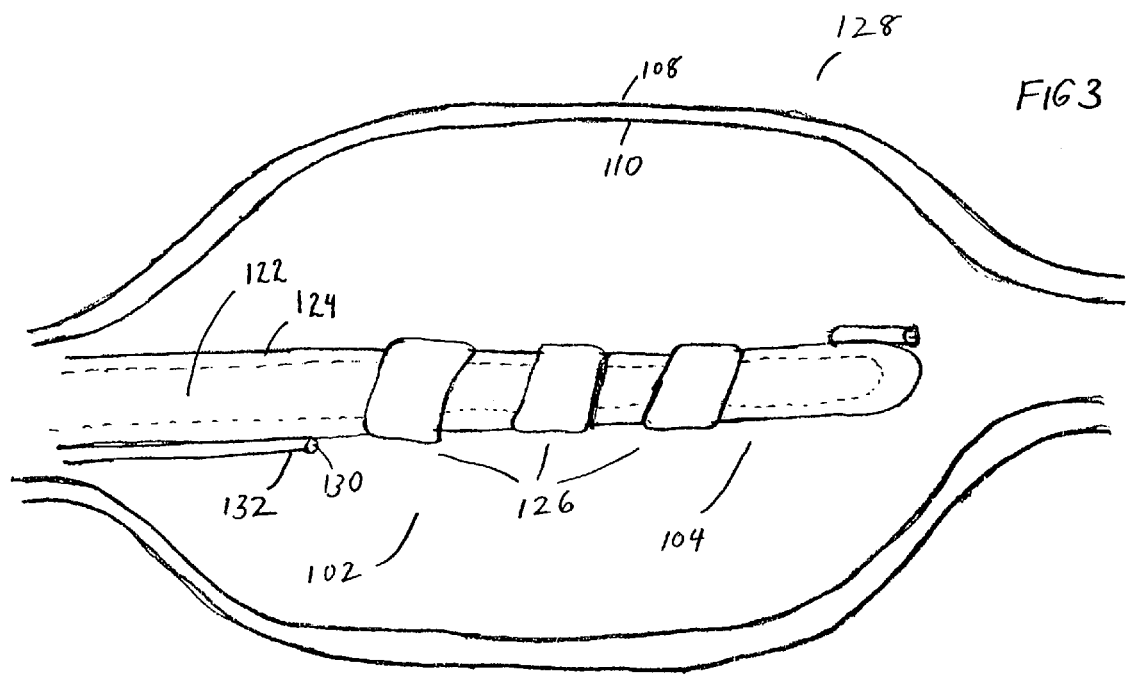
FIG. 3 shows the catheter of FIG. 1 in the lumen, with the lumen insufflated.

In an embodiment, once the catheter 102 is inserted into the lumen 108, the lumen 108 is insufflated. Insufflation is a process by which an internal portion of a body, such as a lumen, is pressurized with a fluid (which may be a gas), thereby increasing the internal volume of the internal portion of the body. FIG. 3 illustrates an insufflation step 128. Insufflation is accomplished by passing an insufflation fluid that may be a gas or a liquid under pressure into the lumen 108 from outside the lumen. Insufflation pressure is generally kept low to maintain patient safety. In one embodiment, the insufflation pressure is between 0.1 and 0.3 psig. Any means compatible with a surgical procedure may be used to insufflate the lumen 108. In an embodiment, the insufflation fluid is air. In another embodiment, the insufflation fluid is an optically transparent liquid. In yet another embodiment, the insufflation fluid is a light-scattering liquid. In an embodiment, the insufflation fluid enters the lumen 108 through an insufflation passage 130 along the catheter body 104. In an embodiment, the insufflation passage comprises a tube 132 external to the catheter body 104, as shown in FIG. 3. In another embodiment, an insufflation tube is internal to the catheter body 104, with an outlet provided through the catheter wall 124 into the lumen 108. In yet another embodiment, the at least one internal longitudinal passage 122 through the catheter body 104 serves multiple functions including insufflation. In still another embodiment, the phototherapy procedure is performed without insufflation of the lumen 108.

Figure 4:
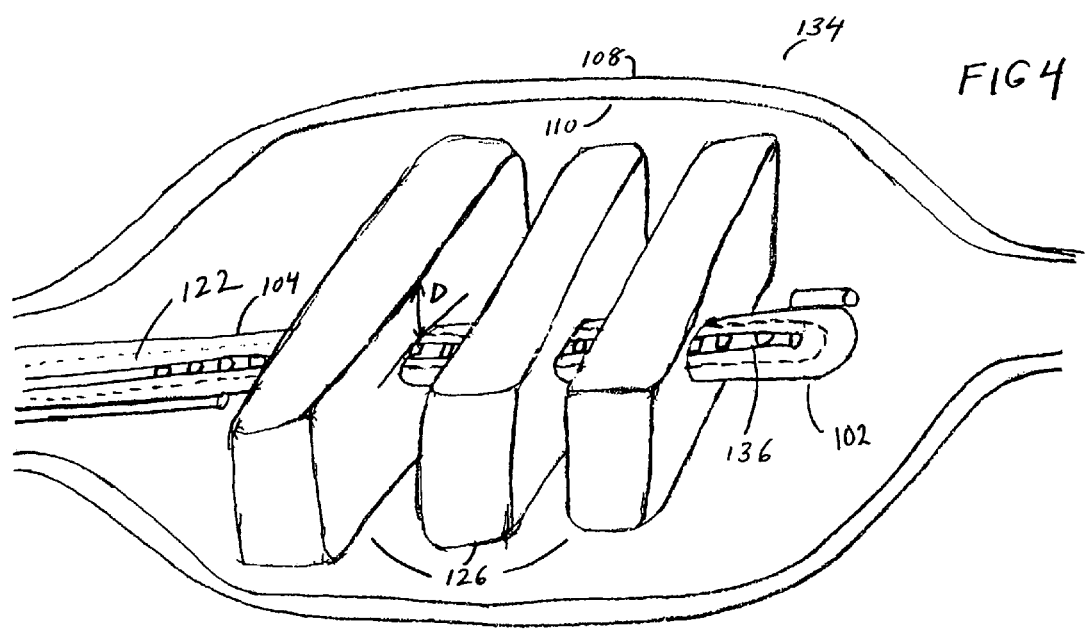
FIG. 4 shows the catheter of FIG. 1 in the insufflated lumen, with distancing members deployed.

The one or more distancing members 126 are shown undeployed in FIG. 3. In an embodiment, the one or more distancing members 126 are deployed after the lumen 108 is insufflated. FIG. 4 illustrates deployment 134 of the one or more distancing members 126 in the lumen 108. In an embodiment, at least one of the one or more distancing members 126 comprises a balloon. Deployed, the one or more distancing members 126 maintain a minimum distance D between the catheter body 104 or a device positioned within the catheter body 104 and the lumen wall 110. In an embodiment, deployment of a distancing member 126 comprises moving at least a portion of the distancing member 126 from an undeployed position close to the catheter body 104 to a deployed position further from the catheter body 104 in a direction transverse to the catheter body and the at least one internal longitudinal passage 122. In an embodiment, the catheter body 104 includes a light-emitting device 136 positioned in the at least one internal longitudinal passage 122 and the minimum distance D determines a corresponding maximum intensity of light reaching the lumen wall 110 from the light-emitting device 136. A radiation emitting device may be substituted for the light emitting device 136 herein.

In a phototherapy application, the minimum distance D between a catheter body and a lumen wall may depend upon a variety of factors including the optical power, wavelength, and distribution of light emitted by the light-emitting device. The minimum distance D may also depend upon dosing requirements for a particular phototherapeutic procedure, which may be determined for an individual patient and the particular tissue and condition being treated. D is used herein to generically represent a minimum distance established between a catheter body and a lumen wall or other body tissue surface by any distancing member of the present invention, and does not represent a specific distance. The minimum distance D may also be a measure of the distance between a light source or any other device within (or associated with) the catheter and the lumen wall.

In an embodiment, the distancing member 126 has a substantially fixed physical extent of deployment that provides a minimum distance D. In an embodiment, the distancing member 126 having a substantially fixed physical extent of deployment includes a balloon. In an embodiment, the balloon is fabricated from a substantially inelastic material. In another embodiment, deployment of the one or more distancing members 126 is adjustable so that the one or more distancing members 126 may provide a range of minimum distances D for the specific requirements of a medical procedure. For example, a distancing member 126 may be deployed in a fully deployed state or in a range of partially deployed states in order to provide a range of minimum distances D. The minimum distance D may be predetermined based on the intended application or use of the catheter. For example, in a phototherapy application, the minimum distance D may be predetermined to provide irradiance within a certain range. Such predetermination may be based on the particular type of application, or more specifically, for a particular type of medical application for a particular patient. In a further embodiment, the minimum distance D is adjustable during a medical procedure, including without limitation, a phototherapy procedure.

In an embodiment, the one or more distancing members 126 surround at least a portion of the length of the catheter body 104 in the lumen 108. In another embodiment, the one or more distancing members 126 are connected to the catheter body 104 at a fixed longitudinal position along the catheter body 104. In yet another embodiment, the one or more distancing members 126 can slide longitudinally relative to the catheter body 104.

In an embodiment, the light-emitting device 136 is positioned in the at least one internal longitudinal passage 122 after the one or more distancing members 126 have been deployed. In another embodiment, the light-emitting device 136 is positioned in the at least one internal longitudinal passage 122 at an earlier step in the phototherapy procedure. In an embodiment, the light-emitting device comprises an optical fiber coupled proximally to a light source outside the lumen. In another embodiment, the light-emitting device comprises one or more light-emitting diodes.

The one or more distancing members 126 are preferably constructed of biocompatible materials and may be any type or combination of types of distancing member compatible with deployment within the lumen 108. In one embodiment, the one or more distancing member is a plurality of balloons. The plurality of balloons may be of any physical configuration and number that provide the minimum distance D between the catheter body 104 and the lumen wall 108, and are adapted for inflation with a pressurized fluid that may be a liquid or a gas. In an embodiment, the fluid is air. In another embodiment, the fluid is an optically transparent liquid. In yet another embodiment, the fluid is a light-scattering liquid.

In an embodiment, the plurality of balloons are made from polyurethane and the inflation pressure is substantially in the range from about 0.5 to about 0.75 psig (pounds per square inch gauge). In another embodiment, the one or more distancing members 126 comprise a plurality of flexible members extendable from the catheter body 104. In yet another embodiment, the one or more distancing members 126 comprise a plurality of jointed arms that are extendable from the catheter body 104. Still other embodiments include combinations of one or more balloon, flexible members, and jointed members.

Depending on the construction of the one or more distancing members 126, deployment may comprise inflation of one or more balloons through a tube external or internal to the catheter body 104, longitudinal sliding of a mechanical linkage along the catheter body 104 for flexion members or jointed arms, or another means. In one embodiment, the one or more distancing members 126 comprise a plurality of balloons, and deployment comprises passing pressurized fluid into one or more of the plurality of balloons through one or more inflation passages positioned along the catheter body 104. In an embodiment, the one or more inflation passages are internal to the catheter body 104 and include openings through the catheter body 104 in fluid connection with the one or more balloons. In another embodiment, the one or more inflation passages comprise one or more tubes external to the catheter body 104.

In the embodiment of FIG. 4, the deployed one or more distancing members 126 do not entirely fill the insufflated lumen 108. Rather, the deployed one or more distancing members 126 establish the minimum distance D between the catheter body 104 and the lumen wall 110, beyond which the catheter 102 with the deployed distancing members 126 is free to move within the lumen 108. In an embodiment, at least one of the one or more distancing members 126 comprises a balloon. In an embodiment, the balloon is substantially transparent to phototherapeutic light. In another embodiment, a portion of the balloon is substantially optically reflective. In yet another embodiment, a portion of the balloon substantially scatters light. In still another embodiment, the balloon is patterned with respect to its optical properties, thereby substantially determining a distribution of light intensity reaching the lumen wall 110 from the light-emitting device 136. In an embodiment of a phototherapy procedure according to the present invention, light emitted from the light-emitting device 136 treats a bacterial infection in the lumen wall 110 with the use of photosensitizers and without the use of photosensitizers. In an embodiment, radiation emitted from a radiation-emitting device treats a cancerous or precancerous condition.

FIG. 5a through FIG. 7b illustrate embodiments of distancing members of the present invention, with each of the figures illustrating a single distancing member along a section of a catheter. Catheters of the present invention preferably include one or more distancing members, and may include combinations of types of distancing members, including those illustrated in FIG. 5a through FIG. 7b, or other mechanisms or devices that establish a minimum distance between a catheter body and a lumen wall.

FIG. 5a illustrates an embodiment of a deployed balloon-type distancing member 150 of the present invention, including a balloon 152 surrounding and deployed (inflated) about a longitudinal section of a catheter body 154. The catheter body 154 includes at least one longitudinal passage 156 and a catheter wall 158. The balloon 152 is inflated and deflated through one of the at least one longitudinal passages 156 extending at least proximally of the balloon 152 along the catheter body 154. In an embodiment, the balloon 152 is inflated and deflated through an internal longitudinal passage 160 along the catheter and a transverse portal 162 between the passage 160 and the interior of the balloon 152. In another embodiment, the balloon 152 is inflated and deflated through a tube positioned external to the catheter body 154.

The balloon 152 may be of any size and shape suitable for deployment as a distancing member in a lumen. In an embodiment, the balloon 152 has a shape that parallels the shape of the lumen. In one embodiment, the balloon 152 is substantially cylindrical. In another embodiment, the balloon 152 is substantially spherical. In yet another embodiment, the balloon 152 is substantially conical in cross section. In still another embodiment, the balloon 152 is substantially rectangular in cross section. The balloon 152 is preferably made of a flexible biocompatible material. In one embodiment, the balloon 152 has a predefined inflated shape. In another embodiment, the balloon 152 is elastomeric. Materials for the construction of balloons of the present invention preferably include polyurethane, polyethylene terephthalate (PET), polyethylene, polypropylene, polyesters and fluoropolymers.

FIG. 5b illustrates an embodiment of an undeployed balloon-type distancing member 164 of the present invention. The balloon 152 is shown in FIG. 5b in an undeployed (deflated) state 166, the undeployed state 166 providing a reduced cross section for insertion and removal of the catheter body 154 and balloon 152 from a lumen through an orifice.

FIG. 6a illustrates an embodiment of a deployed flexible member-type distancing member 168 of the present invention, the distancing member 168 comprising a plurality of flexible members 170 deployed (expanded by flexion) in a circumferential array about a longitudinal section of a catheter body 172. The plurality of flexible members 170 may include any number of flexible members circumferentially distributed about the catheter body 172. In an embodiment, the plurality of flexible members 170 includes three flexible members. In another embodiment, the plurality of flexible members 170 includes four flexible members. In yet another embodiment, the plurality of flexible members 170 includes at least six flexible members.

The distancing member 168 is preferably deployed via a proximal mechanical linkage 174 for activation by a surgeon. The plurality of flexible members 170 are preferably made of a flexible biocompatible material having elastic and structural properties suitable for reliable transverse extension from and retraction to the catheter body 172. Suitable materials include biocompatible plastics and surgical steels. The plurality of flexible members 170 may be adapted to be blades, wires, tubes, or any other mechanical shape compatible with reversible deployment from the catheter body 172. In an embodiment, the plurality of flexible members 170 are optically transparent. In another embodiment, the plurality of flexible members 170 are optically reflective. In still another embodiment, the plurality of flexible members 170 comprises one or more light-emitting devices.

FIG. 6b illustrates an embodiment of an undeployed flexible member-type distancing member 176 of the present invention. The plurality of flexible members 170 of FIG. 6a are shown in an undeployed position 178, that is, transversely retracted toward the catheter body. The undeployed position 178 provides a reduced cross section for insertion and removal of the catheter body 172 and plurality of flexible members 170 from a lumen through an orifice.

FIG. 7a illustrates an embodiment of a deployed jointed arm-type distancing member 180 of the present invention, the distancing member 180 comprising a plurality of jointed arms 182 deployed (transversely extended) in a circumferential array about a longitudinal section of a catheter body 184. The plurality of jointed arms 182 may include any number of jointed arms 182 circumferentially distributed about the catheter body 184. In an embodiment, the plurality of jointed arms 182 includes three jointed arms. In another embodiment, the plurality of jointed arms 182 includes four jointed arms. In yet another embodiment, the plurality of jointed arms 182 includes at least six jointed arms. The distancing member 180 may be deployed via a proximal mechanical linkage 185 for activation by a surgeon. Each of the plurality of jointed arms 182 includes two or more segments 186 coupled together by one or more hinge members 187. In an embodiment, the one or more hinge members comprises a flexible joint between two adjacent segments 186. In an embodiment, deployment of the distancing member 180 comprises flexion of one or more of the one or more hinge members.

The plurality of jointed arms 182 are preferably made of biocompatible materials having elastic and structural properties suitable for reliable transverse extension from and retraction to the catheter body 184. Suitable materials include without limitation biocompatible plastics, ceramics and surgical steels. In an embodiment, the plurality of jointed arms 182 are optically transparent. In another embodiment, the plurality of jointed arms 182 are optically reflective. In still another embodiment, the plurality of jointed arms 182 comprises one or more light-emitting devices.

FIG. 7b illustrates an embodiment of an undeployed jointed arm-type distancing member 188 of the present invention. The plurality of jointed arms 182 of FIG. 7b are shown in an undeployed position 190, that is, transversely retracted toward the catheter body 184. The undeployed position 190 provides a reduced cross section for insertion and removal of the catheter body 184 and the plurality of jointed arms 182 from a lumen through an orifice.

Longitudinal passages through embodiments of catheters of the present invention may be any type of longitudinal passage. In an embodiment, a longitudinal passage may be a longitudinal bore formed in a catheter body. In other embodiments, a plurality of independent longitudinal bores may be formed in a catheter body. In still other embodiments, longitudinal passages may be defined by structural components of a catheter body. FIG. 8 illustrates an embodiment of a catheter 191 of the present invention, in axial view. The catheter is seen to have a catheter body 192 having an outer sheath 193, a central member 194 within the sheath 193, and a length of longitudinally split tubing 195 that defines a longitudinal passage 196 between the outer sheath 193 and the central member 194 along the catheter. That is, there is a gap in the circumference of the tubing 195. In an embodiment, the longitudinally split tubing 195 may be referred to as "c-cut" tubing. In an embodiment, the central member 194 is a length of tubing. In another embodiment, the central member 194 includes a light-emitting device for phototherapy. In yet another embodiment, the central member 194 is another type of medical device.

FIG. 9a illustrates in an undeployed state 197 yet another embodiment of a catheter 198 of the present invention. The catheter 198 has a catheter body 199 about which a distancing member 200 can be deployed. The distancing member 200 includes a plurality of flexible members 201 that in an embodiment resemble the plurality of flexible members 170 illustrated in FIG. 6a and FIG. 6b. The distancing member 200 also includes at least one balloon 202, shown in a deflated state in FIG. 9a. FIG. 9b illustrates the catheter 198 in a deployed state 203 in which the at least one balloon 202 has been inflated, thereby forcing the plurality of flexible members 20i outward from the catheter body 199 to establish the minimum distance D. In an embodiment, the distancing member 200 also includes a sliding member 204 that can reversibly move longitudinally along the catheter body as the distancing member 200 is deployed, thereby accommodating a decreased longitudinal extent of the distancing member 200 along the catheter body 199 with deployment.

Embodiments of distancing members of the present invention may be adapted so that they do not significantly deform when deployed and used in a particular environment and application. For example, such distancing members may be adapted so they do not significantly deform when in contact with or pressed against a lumen wall. Such adaptation may be achieved by, for example, utilization of polyethylene terephthalate (PET) material in the construction of balloon type distancing members. Alternatively, embodiments of distancing members may be adapted to deform only a certain amount based on the anticipated pressures and forces in the environment in which the distancing members are intended to be used in a particular application. For example, such distancing members may be adapted so that they may deform when in contact with or pressed against a lumen wall, but do not deform so much that the distance between the lumen wall and the catheter body is less than the minimum distance D. Such adaptation may be achieved by, for example, utilization of polyurethane type material in the construction of balloon type catheters.

FIG. 10a illustrates an embodiment of a sheathed catheter 206 of the present invention including a catheter body 208, and a plurality of (undeployed) distancing members 210, at least partially surrounded by an insertion sheath 212. In an embodiment, the insertion sheath 212 encloses the undeployed distancing members 210 during insertion of the catheter into a lumen. In an embodiment, the insertion sheath 212 encloses the undeployed distancing members 210 during removal of the catheter from a lumen. An insertion sheath 212 may protect body tissues during insertion or removal of a catheter 206 from a lumen. An insertion sheath 212 may also ensure proper operation of the distancing members after insertion. The insertion sheath 212 is preferably made from a flexible biocompatible material and is adapted to slidably fit over the catheter body 208 and the undeployed distancing members 210.

FIG. 10b shows an embodiment of an unsheathed catheter 214, where the sheath 212 has been retracted from at least a portion of the catheter body 208 and from a portion 216 of the plurality of distancing members 210 of FIG. 10a. FIG. 10c shows a deployed sheathed catheter 218 wherein the portion 216 of the plurality of distancing members 210 from which the sheath 212 has been retracted is deployed. In an embodiment, the plurality of distancing members 210 comprises a plurality of balloons. In another embodiment, the plurality of distancing members comprises a plurality of flexible members. In yet another embodiment, the plurality of distancing members comprises a plurality of jointed arms. In an embodiment, the sheath 212 is retracted from all of the plurality of distancing members. In another embodiment, the sheath 212 is extended to cover the plurality of distancing members following a medical procedure.

Embodiments of catheters of the present invention allow for motion of the catheter within a lumen during a phototherapy procedure. FIG. 11a and FIG. 11b illustrate an embodiment of a catheter 220 of the present invention being used in a phototherapy procedure within a lumen 222 having a lumen wall 224 and experiencing peristalsis. In an embodiment, peristaltic motion of the lumen continues substantially undisturbed during a phototherapy procedure. In another embodiment, time-averaged repositioning of the catheter 220 in the lumen 222 due to peristalsis during a phototherapy procedure enhances the homogeneity of light dosing at the lumen wall 224. Motion of a catheter 220 within a lumen 222 due to peristalsis or other natural motion of a lumen is described herein as passive motion of the catheter 220. The catheter 220 has a flexible catheter body 226, distal balloon 228, a proximal balloon 230 and a longitudinal axis 232. The catheter also includes a longitudinal passage 234 in which is positioned a light-emitting device 236. In an embodiment, the light-emitting device comprises an optical fiber proximally coupled to a light source outside the lumen. In another embodiment, the light-emitting device comprises at least one light-emitting diode.

Each of the distal balloon 228 and the proximal balloon 230 is adapted to provide a minimum distance D between the catheter body 226 and the lumen wall 224. In FIG. 11a, the distal balloon 228 is substantially free to move transversely to the axis 232 within a first portion 238 of the lumen 222. In a second portion 240 of the lumen 222, the proximal balloon 230 is repositioned by muscular contraction of the lumen 222, with the proximal balloon 230 maintaining the minimum distance D from lumen wall 224. FIG. 11b illustrates the lumen 222 and catheter 220 of FIG. 11a at a different time, at which the proximal balloon 230 is substantially free to move transversely to the axis 232 within the second portion 240 of the lumen 222, and the distal balloon 228 is repositioned by muscular contraction of the lumen 222, with the distal balloon 228 maintaining the minimum distance D from the lumen wall 224. In an embodiment, at least one of the distal balloon 228 and the proximal balloon 230 transiently occlude the lumen 222 during peristaltic movement of the lumen 222. In another embodiment, a phototherapy treatment is conducted during peristalsis of the lumen 222. In an embodiment, the motion of the catheter 220 in response to peristalsis enhances the homogeneity of light dose reaching the lumen wall 224.

A catheter of the present invention may also be adapted for accentuating displacement within a lumen in response to motion of the lumen. FIG. 12a through FIG. 12c illustrate another embodiment of a catheter 250 of the present invention having a flexible catheter body 252 including a light-emitting device 254, a longitudinal axis 256 and a plurality of distancing members 258. The distancing members 258 are adapted to enhance the homogeneity of a radiation dose during a phototherapy procedure within a lumen 260 having a muscular lumen wall 262. FIG. 12a illustrates the catheter 250 in the lumen 260 with the lumen wall 262 relaxed, showing approximate centering of the catheter 250 transverse to the axis 256. FIG. 12b illustrates contraction of a first portion 264 of the lumen 260 during peristalsis, displacing the catheter body 252 transversely off-center in a first direction 266. FIG. 12c illustrates contraction of a second portion 268 of the lumen 260 during peristalsis, displacing the catheter body 252 transversely off-center in a second direction 270.

In addition to experiencing passive displacement within a lumen in response to natural body motions during a medical procedure (passive modulation of the position of a catheter), catheters of the present invention can be moved actively within the lumen as part of a procedure, for example, by physical manipulation of the catheter by a surgeon, or through use of a positional control system. Any type of positional control may be used, for example vibration, rotation, translation, or inflation and deflation of balloon members.

Any motion of a catheter during medical and other procedures, whether active or passive, may be described herein as modulation of the position of the catheter, or modulating the position of the catheter. In an embodiment, modulation of the position of a catheter during a phototherapy procedure enhances the homogeneity of dose delivery of light to the interior of a lumen. In another embodiment, modulation of the position of a catheter during a phototherapy procedure moves the catheter about the interior of a lumen in a pattern of motion adapted to control a dose of light delivered to one or more specific portion of a lumen wall. In a further embodiment, the modulation is periodic about a nominal location of the catheter within the lumen. Periodic, aperiodic, random, passive or active motion of a catheter may also be referred to as "dithering" the catheter.

Figure 13:
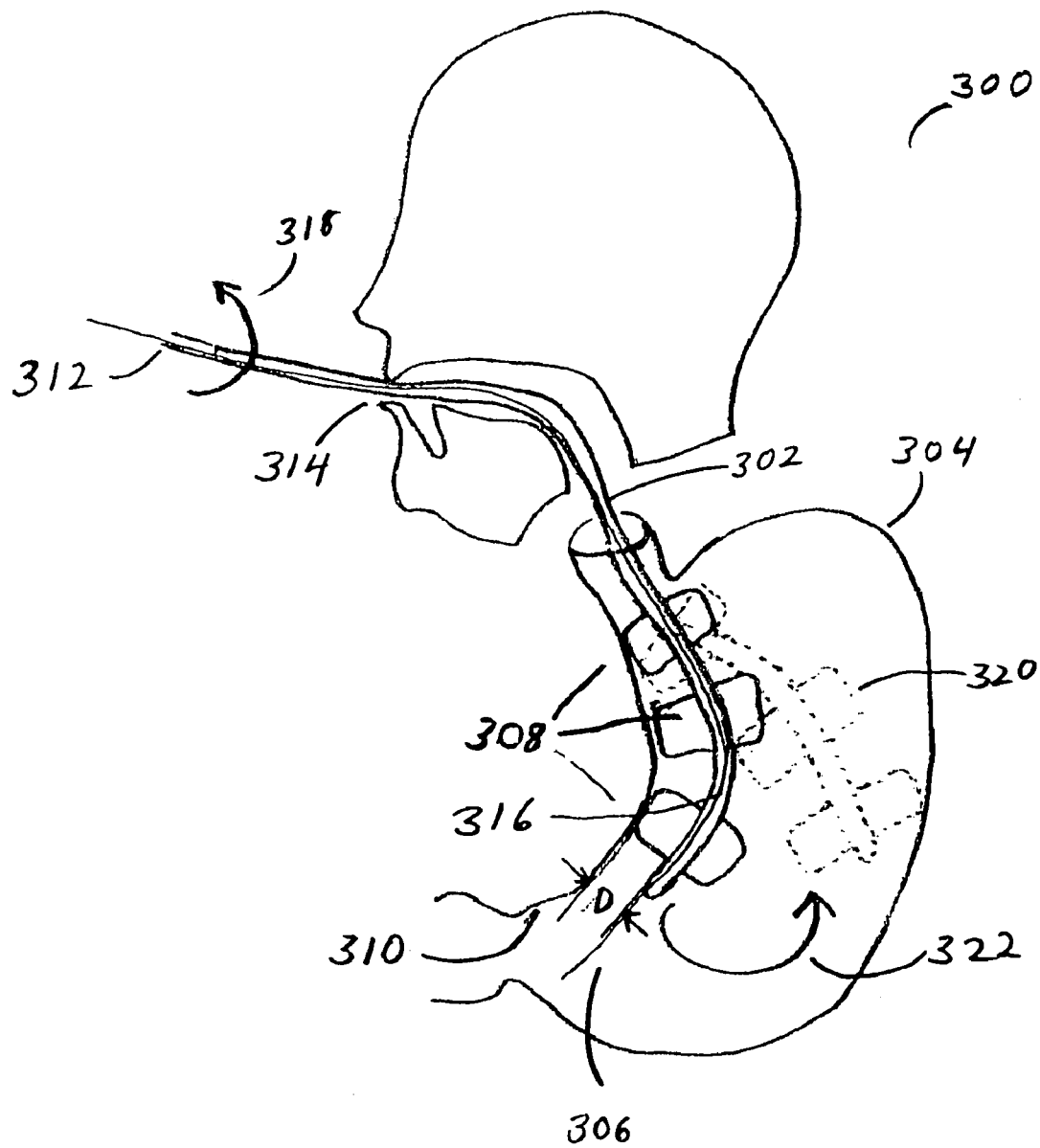
FIG. 13 illustrates an embodiment of a phototherapy procedure of the present invention wherein a catheter is actively rotated to modulate its position in a lumen.

FIG. 13 illustrates an embodiment of a phototherapy procedure 300 of the present invention during which a catheter 302 of the present invention is actively moved within a lumen 304. In one embodiment, the lumen 304 is a stomach. In another embodiment, the lumen 304 is another part of a digestive tract. The catheter 302 is seen to have a distal end 306 positioned within the lumen 304 and a plurality of deployed distancing members 308 adapted to maintain a minimum distance D from a lumen wall 310. The catheter is also seen to have a proximal end 312 extending from a body orifice 314, and a longitudinal axis 316. In an embodiment, the body orifice 314 is a mouth. In another embodiment, the body orifice 314 is a nose. In the procedure 300, catheter 302 is rotated or twisted 318 about the longitudinal axis 316 substantially at the proximal end 312, inducing a distal portion 320 of the catheter 302 to rotate or twist 322 and reposition (modulate its position) within the lumen 304.

In an embodiment, the rotating or twisting of the catheter 302 is performed manually by a surgeon. In another embodiment, the rotating or twisting of the catheter 302 is performed by a catheter control system. In an embodiment, the catheter control system is automated. This modulation of the position of the catheter 302 within the lumen 304 may enhance the homogeneity of light dosing to the lumen wall 310 during the phototherapy procedure. In an embodiment, the modulation of the position of the catheter 302 decreases the time required to perform a phototherapy procedure relative to the time required without modulation.

Figure 14:
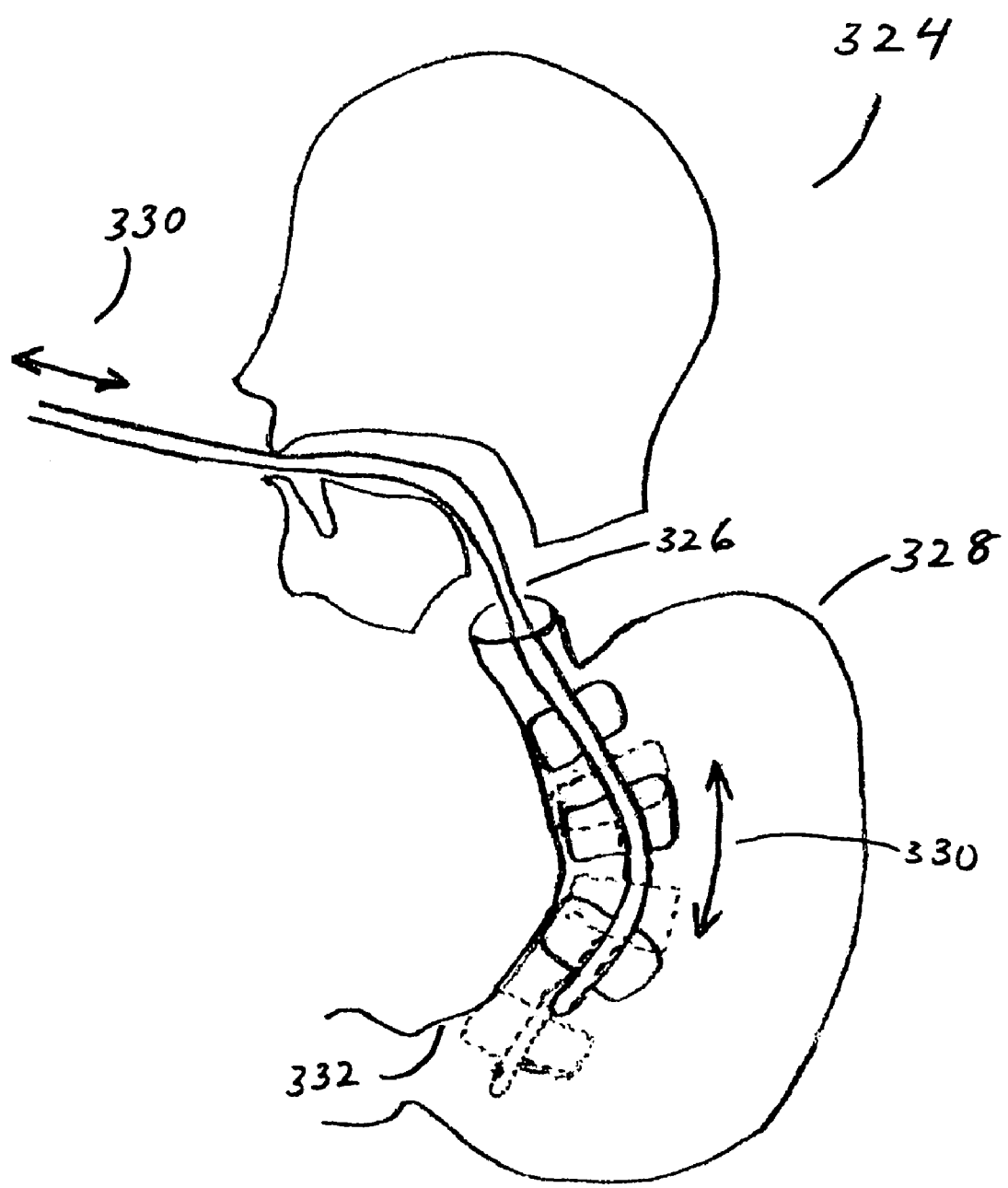
FIG. 14 illustrates an embodiment of a phototherapy procedure of the present invention wherein a catheter is translated longitudinally to modulate its position in a lumen.

FIG. 14 illustrates another embodiment of a phototherapy procedure 324 of the present invention during which the position of a catheter 326 of the present invention is modulated within a lumen 328. The procedure of FIG. 14 resembles the procedure of FIG. 13 except that the catheter 326 of FIG. 14 is adapted for longitudinal modulation 330, as opposed to the rotational modulation illustrated in FIG. 13. In an embodiment, the longitudinal modulation 330 of the position of the catheter 326 is performed manually by a surgeon. In another embodiment, the longitudinal modulation 330 of the catheter position is performed by a catheter control mechanism. In an embodiment, the catheter control mechanism is automated. In another embodiment, the modulation is a combination of rotational and longitudinal motion of the catheter 326. In an embodiment, the modulation of the position of the catheter 326 within the lumen 328 enhances the homogeneity of light dosing to a lumen wall 332 during the phototherapy procedure. In another embodiment, the modulation of the position of the catheter 326 within the lumen 328 modifies the dose of light received by a specific portion of the lumen wall 332 relative to other portions of the lumen wall 332 by controlling the duration of irradiation at the specific portion of the lumen wall. In an embodiment, the modulation of the position of the catheter 326 decreases the time required to perform a phototherapy procedure relative to the time required without modulation.

FIG. 15a and FIG. 15b illustrate in axial view another embodiment of a method 350 and a catheter 352 of the present invention including modulating the position of the catheter 352 within a lumen 354 having a lumen wall 356. The catheter 352 includes a catheter body 358 having a longitudinal axis 360 and a longitudinal passage 362 enclosing a light-emitting device is 364. A balloon 366 is eccentrically deployed about the catheter body 358 as a distancing member adapted to maintain a minimum distance D between the catheter body 358 and the lumen wall 356. The catheter 352 is also adapted for rotation or twisting 368 substantially about the axis 360 during a phototherapy procedure. Rotation or twisting of the catheter 352 causes the catheter body 358 and the light-emitting device 364 to change position at least transversely to the axis 360.

FIG. 15a shows the catheter 352 in a first rotational orientation and first transverse position 370 within the lumen 354, and FIG. 15b shows the catheter 352 in a second rotational orientation and second transverse position 372 within the lumen 354. Continued rotation of the catheter 352 during the phototherapy procedure 350 may provide a cam-type motion that may enhance the homogeneity of light dose delivery to the lumen wall 356, while maintaining the minimum distance D between the catheter body 358 including the light-emitting device 364 and the lumen wall 356.

FIG. 16a and FIG. 16b illustrate in axial view yet another embodiment of a method 400 and catheter 402 of the present invention for modulating the position of the catheter 402 during a phototherapy procedure within a lumen 404 having a lumen wall 406. The catheter 402 includes a catheter body 408 having a longitudinal axis 410 and a longitudinal passage 412 enclosing a light-emitting device 414. At least one central distancing member 416 is deployed about the catheter body 408 to maintain a minimum distance D between the catheter body 408 and the lumen wall 406. A plurality of peripheral distancing members 418 is arrayed about the at least one central distancing member 416. Selective control of deployment of the plurality of peripheral distancing members 418 actively positions the catheter 402 within the lumen 404. In an embodiment, at least one of the central distancing members 416 and the plurality of peripheral distancing members 418 is a balloon. In another embodiment, at least one of the central distancing members 416 and the plurality of peripheral distancing members 418 is a plurality of expandable flexion members. In yet another embodiment, at least one of the central distancing members 416 and the plurality of peripheral distancing members 418 is a plurality of expandable jointed arms.

In an embodiment, each of the plurality of peripheral distancing members 418 is independently deployable. In an embodiment, deployment of one or more of the plurality of independently deployable peripheral distancing members is adjustable to one or more positions between undeployed and a maximum deployment. Thus, one of the plurality of independently deployable peripheral distancing members may be more or less deployed than another of the independently deployable peripheral distancing members. In FIG. 16a, a first one 420 of the plurality of peripheral distancing members 418 is less deployed than a second one 422 and a third one 424 of the plurality of peripheral distancing members 418, thereby defining a first position 426 of the catheter 402 within the lumen 404. In FIG. 16b, the third one 424 of the plurality of peripheral distancing members 418 is less deployed than the first one 422 and the second one 424 of the plurality of peripheral distancing members 418, thereby defining a second position 428 of the catheter 402 within the lumen 404 different from the first position 426. In an embodiment, each of the plurality of peripheral distancing members is independently controlled from outside the lumen 404. In another embodiment, the position of the catheter 402 within the lumen is controlled in a periodic manner by modulating the deployment of the plurality of peripheral distancing members 418. In yet another embodiment, the plurality of peripheral distancing members 418 is directly connected to the catheter body 408, without the presence of the central distancing member 416.

Figure 17:
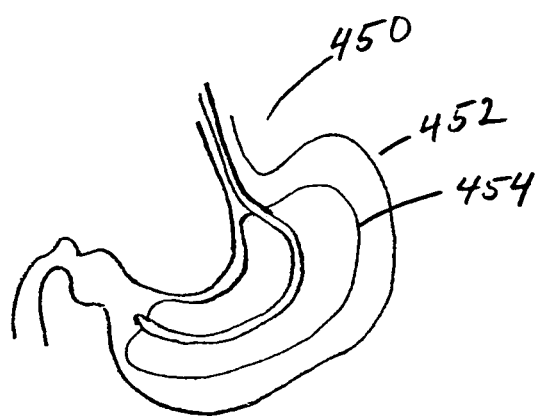
FIG. 17 shows an embodiment of a catheter of the present invention deployed in an insufflated human stomach, where the catheter includes a balloon shaped similarly to and fitting within the insufflated stomach.
Figure 18:
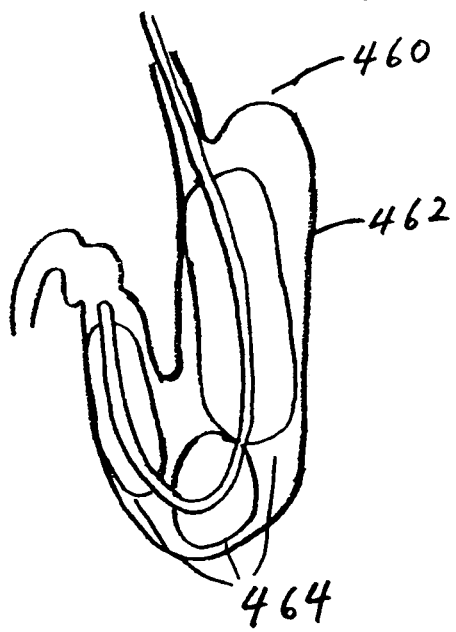
FIG. 18 shows another embodiment of a catheter of the present invention deployed in an insufflated human stomach, where the catheter includes a plurality of deployable members to space the catheter from the wall of the insufflated stomach.

Catheters of the present invention can be used in medical procedures in noncircular, asymmetric, or otherwise irregularly shaped lumens. The human stomach, for example, varies greatly in shape and by over a factor of four or more in volume among adults. FIG. 17 through FIG. 20 illustrate several embodiments of catheters of the present invention adapted for the performance of phototherapy procedures in the human stomach. Each of FIG. 17 through FIG. 20 illustrates a different representative shape of a human stomach. These figures are intended to be illustrative only and by no means comprise an exhaustive compilation of embodiments of the present invention. FIG. 17 illustrates a first catheter 450 deployed in a first insufflated stomach 452. The first catheter 450 includes a single distancing member 454 comprising a balloon having a deployed shape similar to that of the first insufflated stomach 452. FIG. 18 illustrates a second catheter 460 deployed in a second insufflated stomach 462. The second catheter 462 has three distancing members 464 comprising balloons sized for the portion of the second insufflated stomach 462 in which each is deployed. The balloons are spaced apart along the second catheter 460 in a manner that preserves flexibility of the second catheter 460.

Figure 19:
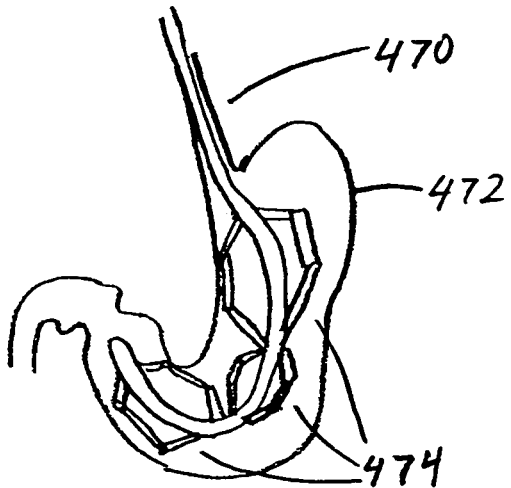
FIG. 19 shows yet another embodiment of a catheter of the present invention deployed in an insufflated human stomach, where the catheter includes a plurality of balloons to space the catheter from the wall of the insufflated stomach.
Figure 20:
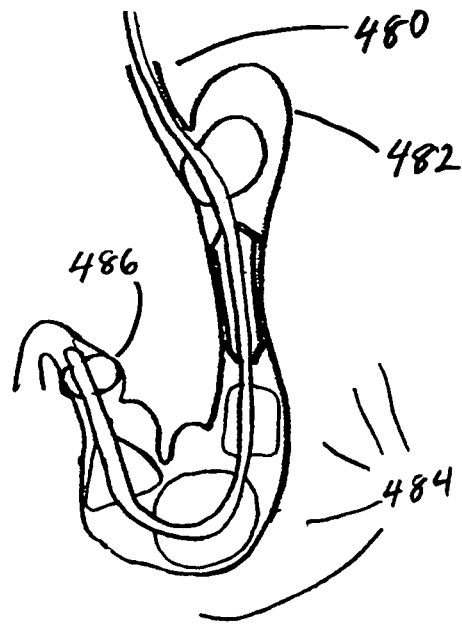
FIG. 20 shows still another embodiment of a catheter of the present invention deployed in an insufflated human stomach, where the catheter includes a combination of plurality of deployable members and balloons to space the catheter from the wall of the insufflated stomach.

FIG. 19 illustrates a third catheter 470 deployed in a third insufflated stomach 472. The third catheter 470 includes three distancing members 474 comprising jointed arms sized for the portion of the third insufflated stomach 472 in which each is deployed. FIG. 20 illustrates a fourth catheter 480 deployed in a fourth insufflated stomach 482. The fourth catheter 480 includes five distancing members 484 comprising a variety of balloons and jointed arms, each adapted for the portion of the fourth insufflated stomach 482 in which it is deployed. In addition, the fourth catheter 480 includes a centering balloon 486 that secures the position of the fourth catheter 480 distally in the fourth stomach 482. In one embodiment, the centering balloon is an occluding balloon. In another embodiment, the centering balloon is a nonoccluding balloon. The distancing members 484 are spaced apart along the fourth catheter 480 to preserve both flexibility of the fourth catheter 480 and to assure that light-emitting portions of the fourth catheter are maintained at least a minimum distance from a surface of the fourth stomach 482.

Figure 22:
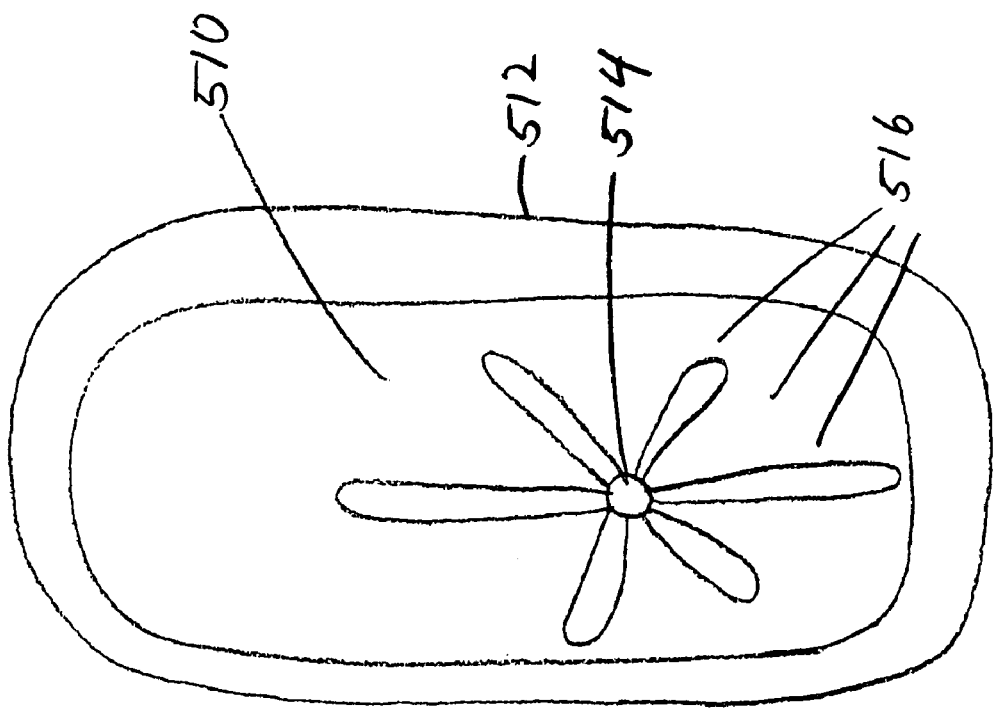
FIG. 22 illustrates another embodiment of a catheter of the present invention having a plurality of distancing members and adapted for phototherapy in a noncircular cross section lumen.
Figure 21:
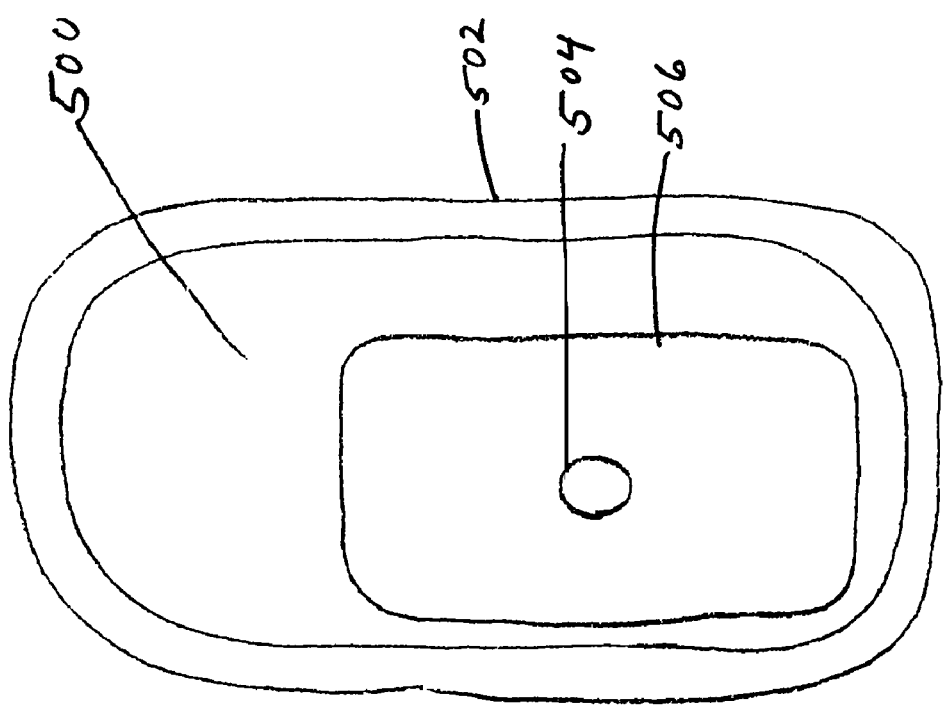
FIG. 21 illustrates an embodiment of a catheter of the present invention having a distancing member adapted for phototherapy in a noncircular cross section lumen.

FIG. 21 illustrates in axial view an embodiment of a catheter 500 of the present invention for deployment in a noncircular lumen 502. The catheter 500 has a catheter body 504 and a distancing member 506 comprising a substantially rectangular cross section balloon. The size and aspect ratio of the rectangular cross section balloon are adapted so the distancing member 506 has a preferred orientation when deployed in the lumen 502, without filling or occluding the lumen 502. FIG. 22 illustrates another catheter 510 of the present invention for deployment in a noncircular lumen 512. The catheter 510 has a catheter body 514 and a circumferential array of distancing members 516. Individual distancing members of the circumferential array 516 are deployed to a variety of distances from the catheter body, thereby generating a preferred orientation of the catheter 510 within the lumen 512. In an embodiment, the distancing members are balloons. In another embodiment, the extent of deployment of individual distancing members is adjustable during a phototherapy procedure.

Figure 23:
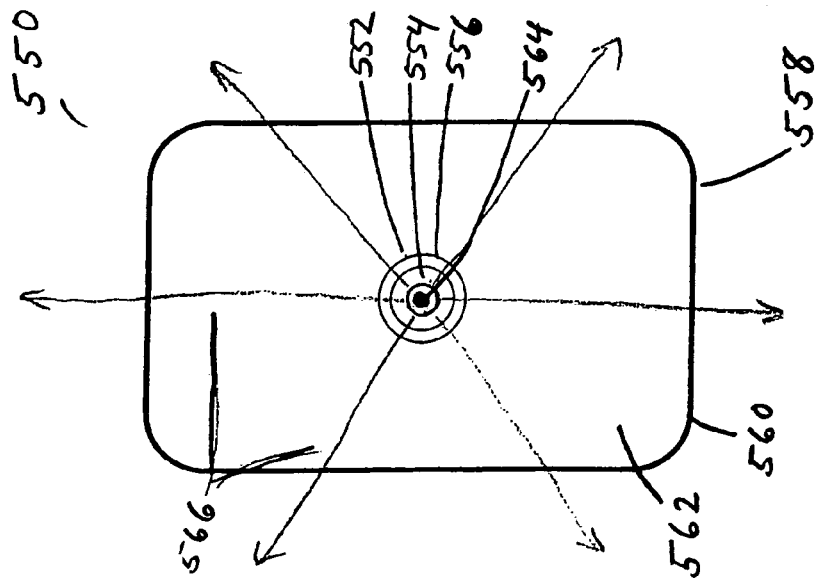
FIG. 23 illustrates an embodiment of a catheter of the present invention for phototherapy.

Embodiments of catheters of the present invention can include means to modify or pattern a distribution of light emitted by a light-emitting device that is positioned within the catheter for a phototherapy procedure. FIG. 23 illustrates in axial view an embodiment of a catheter 550 of the present invention. The catheter 550 includes a catheter body 552 having an internal longitudinal passage 554 and a catheter wall 556. A distancing member comprising a balloon 558 surrounds the catheter body 552. The balloon 558 has a balloon membrane 560 and a balloon volume 562 inflated with a fluid between the balloon membrane 560 and the catheter body 552. In an embodiment, the fluid is a gas. In an embodiment, the gas is air. In an embodiment, the balloon 558 is substantially rectangular in cross section. In another embodiment, the balloon 558 is substantially circular in cross section. In yet another embodiment, the balloon 558 has another cross sectional shape.

A light-emitting device 564 is positioned in the passage 554. In an embodiment, the light-emitting device 564 comprises an optical fiber coupled to a light source located elsewhere. In another embodiment, the light-emitting device comprises at least one light-emitting diode. Light 566 emitted by the light-emitting device 564 is at least partially transmitted through the catheter wall 556 into the balloon volume 562 and toward the balloon membrane 560. In an embodiment, the catheter wall 556 substantially transmits light emitted from the light-emitting device. In another embodiment, the catheter wall 556 substantially scatters light emitted from the light-emitting device. In yet another embodiment, a portion of the catheter wall 556 is at least partially optically reflective. In an embodiment, the balloon wall 560 substantially transmits light emitted from the light-emitting device. In another embodiment, at least a portion of the balloon wall 560 substantially scatters light emitted from the light-emitting device.

Figure 24:
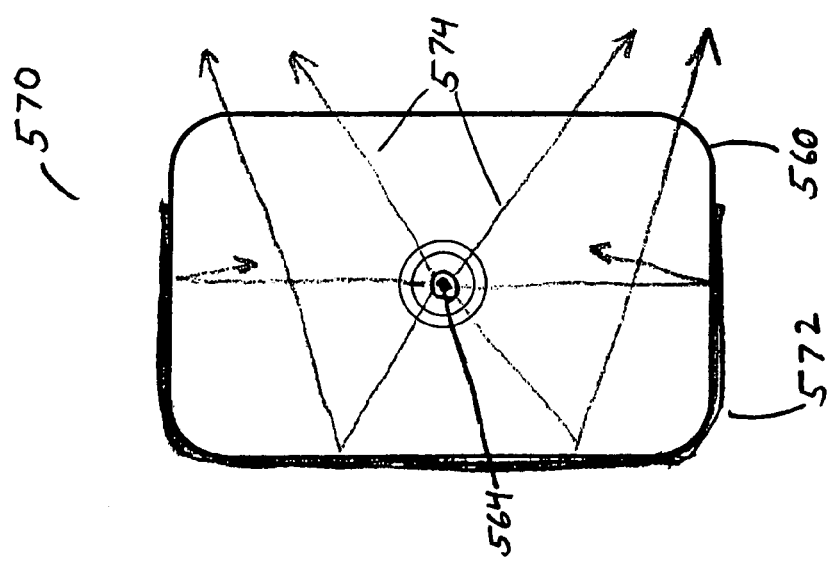
FIG. 24 illustrates an embodiment of a dose-patterning catheter of the present invention.

FIG. 24 illustrates an embodiment of a dose-patterning catheter 570 of the present invention. The dose-patterning catheter 570 resembles the catheter 550 of FIG. 23 with the addition that for dose patterning catheter 570 the balloon membrane 560 includes at least one patterning portion 572 that restricts or redirects the angular range of light 574 emitted from the light-emitting device 564. In an embodiment, the at least one patterning portion 572 is substantially fully reflective. In another embodiment, the at least one patterning portion 572 is partially reflective and partially optically transmissive. In yet another embodiment, the at least one patterning portion 572 is optically scattering. In still another embodiment, the at least one patterning portion 572 is optically absorptive.

Figure 25:
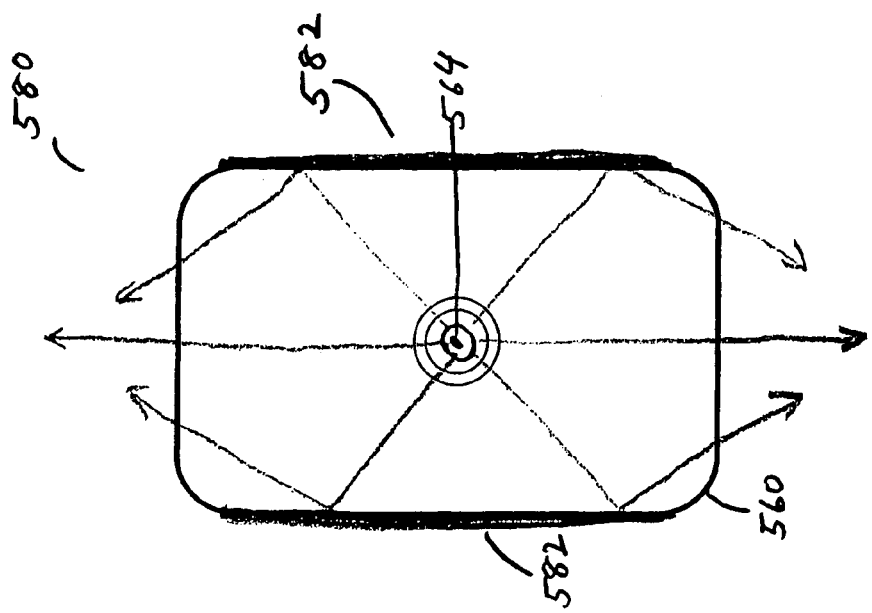
FIG. 25 illustrates another embodiment of a dose-patterning catheter of the present invention.

FIG. 25 illustrates an embodiment of another dose-patterning catheter 580 of the present invention similar to the dose-patterning catheter 570 of FIG. 24, but having a balloon membrane that includes two patterning portion 582. In another embodiment, the dose-patterning catheter 580 includes three or more patterning portions of the balloon membrane 560. In yet another embodiment, the balloon membrane 560 comprises a plurality of dose patterning portions including one or more of reflective, scattering and absorptive portions.

FIG. 26 illustrates yet another embodiment of a dose-patterning catheter 590 of the present invention. The dose-patterning catheter 590 of FIG. 26 is similar to the catheter 550 of FIG. 23, with the exception that the balloon volume 562 of dose patterning catheter 590 is filled with a transparent liquid. In an embodiment, the transparent liquid comprises water. Light 592 emitted from the light-emitting device 564 is transmitted by the catheter wall 556 and the transparent liquid and refracted at the interface with the balloon membrane 560, thereby modifying the dose pattern. In an embodiment, the balloon 558 is adapted to direct the light 592 in a particular direction or pattern using refraction at the balloon membrane 560. FIG. 27 illustrates an embodiment of a windowed dose-patterning catheter 600 of the present invention having a catheter body 602 and a distancing member comprising a balloon 604. The balloon 604 is reflective except for a defined treatment window 606, where it is optically transmissive. In an embodiment, the treatment window is transparent. In another embodiment, the treatment window substantially scatters light.

Figure 28:
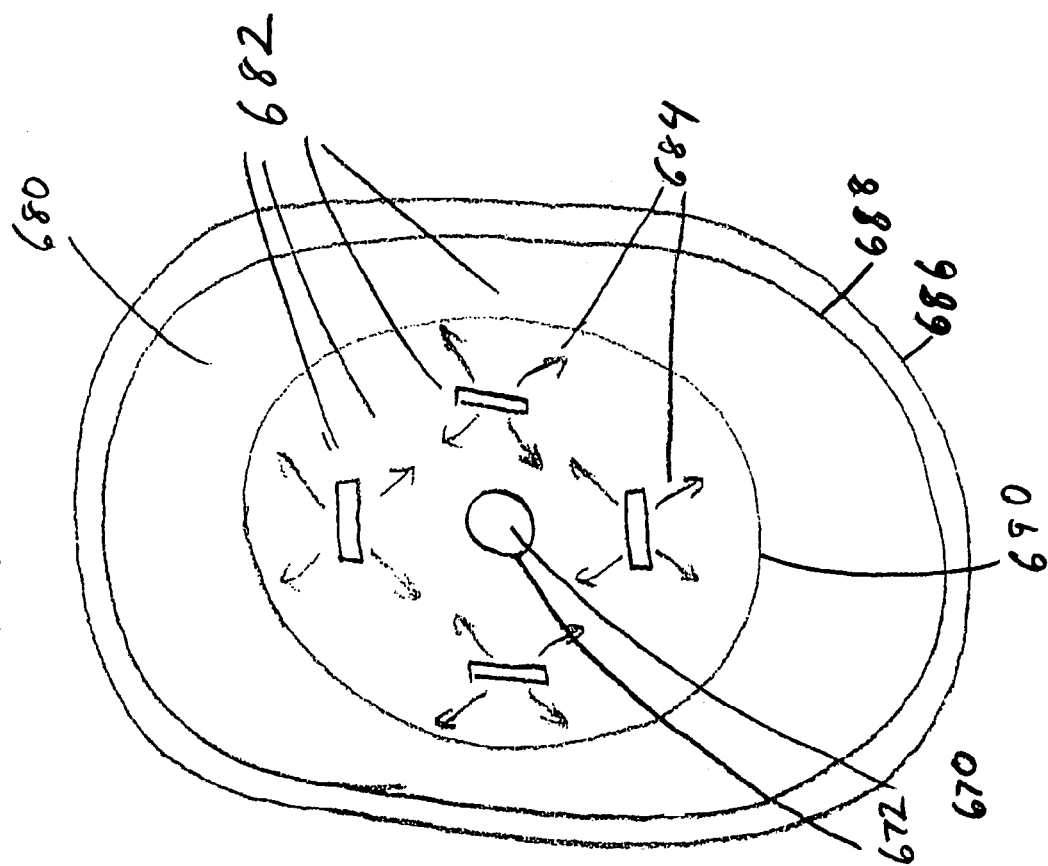
FIG. 28 illustrates an embodiment of a catheter of the present invention wherein distancing members emit light.

FIG. 28 illustrates in axial view an embodiment of a catheter 650 of the present invention having distancing members 652 adapted to emit light 654 for a phototherapy procedure in a lumen 656 having a lumen wall 658. The distancing members 652 may be deployed from a catheter body 670 as illustrated for the deployment of distancing members in any of FIG. 6a through FIG. 7b, or FIG. 9a and FIG. 9b. The catheter body 670 has an outer surface 672. In one embodiment, the distancing members 652 comprise flexible members. In another embodiment, the distancing members 652 comprise jointed arms. The distancing members 652 are adapted to emit light 654 in a pattern. In one embodiment, the distancing members 652 emit light in a direction generally away from a nearest portion of the lumen wall. In an embodiment, the outer surface 672 of the catheter body 670 is reflective.

Figure 29:
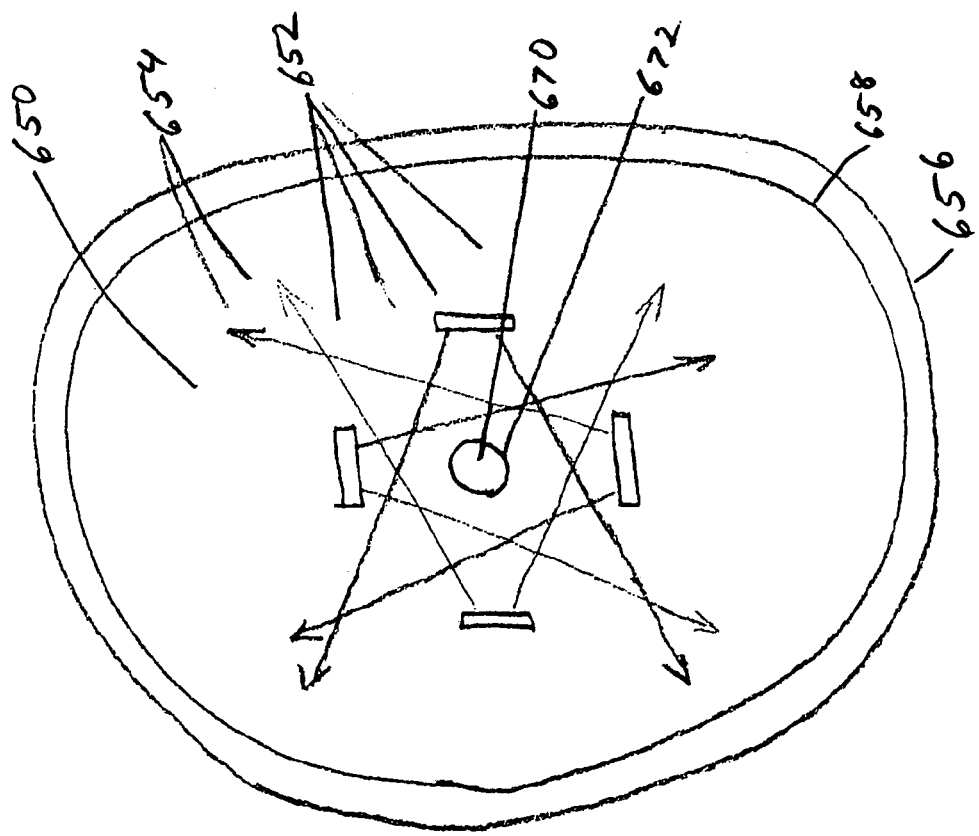
FIG. 29 illustrates another embodiment of a catheter of the present invention wherein distancing members emit light, additionally incorporating a distancing member comprising a balloon.

FIG. 29 illustrates another embodiment of a catheter 680 of the present invention having distancing members 682 adapted the emit light 684 for a phototherapy procedure in a lumen 686 having a lumen wall 688. The catheter of FIG. 29 resembles the catheter of FIG. 28, but differs in the distribution of light 684 from the distancing members 682. The distancing members 682 in the catheter of FIG. 29 emit light substantially isotropically. An additional distancing member comprising a balloon 690 surrounds the light-emitting distancing members 682. In an embodiment, the balloon 690 scatters light emitted by the distancing members 682.

Embodiments of catheters of the present invention may include one or more sensors. The one or more sensors may be used to measure, verify, or provide feedback to establish an extent of deployment of distancing members. Alternatively, the one or more sensors may be used to measure the distance between a sensor and a lumen wall, light intensity or delivered light dose to the lumen wall, or another indicator associated with performance of a procedure that uses the catheter. In an embodiment, the one or more sensors are distance-measuring sensors. In another embodiment, the one or more sensors are pressure sensors. In yet another embodiment, the one or more sensors include light sensors. In still another embodiment, the one or more sensors provide visualization means for the interior of the lumen. In a further embodiment, the visualization means includes an imaging optical fiber. In another embodiment, the visualization means includes an electronic imaging sensor. In an embodiment, the imaging sensor is a single-chip (integrated circuit) camera. Sensors in embodiments of catheters of the present invention may be connected to instrumentation outside the lumen using optical fibers, electrical connections, hollow tubes (for example, for some types of pressure sensors), or by radio-frequency coupling. In an embodiment, a catheter of the present invention includes no sensors.

Figure 30A:
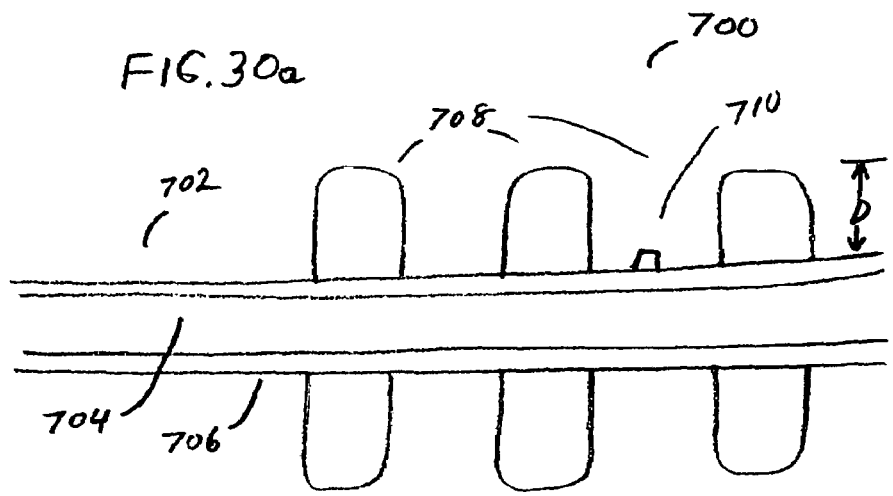
FIG. 30a through FIG. 30d illustrate exemplary embodiments of the positioning of sensors with a catheter of the present invention.
Figure 30B:
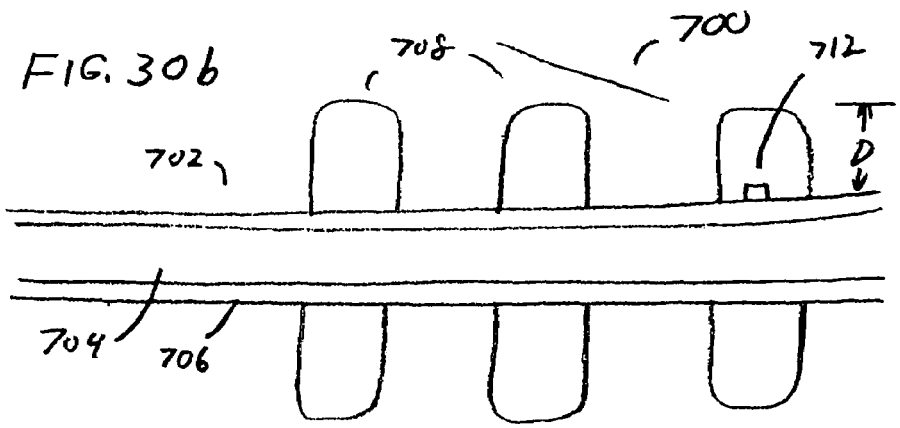
Figure 30C:
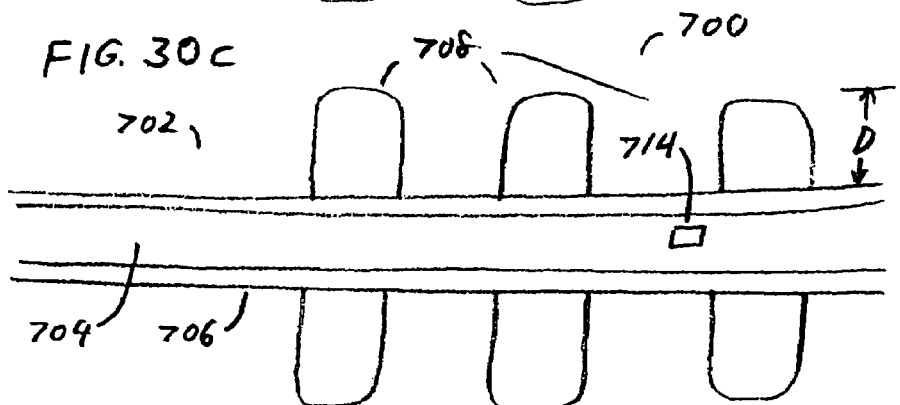
Figure 30D:
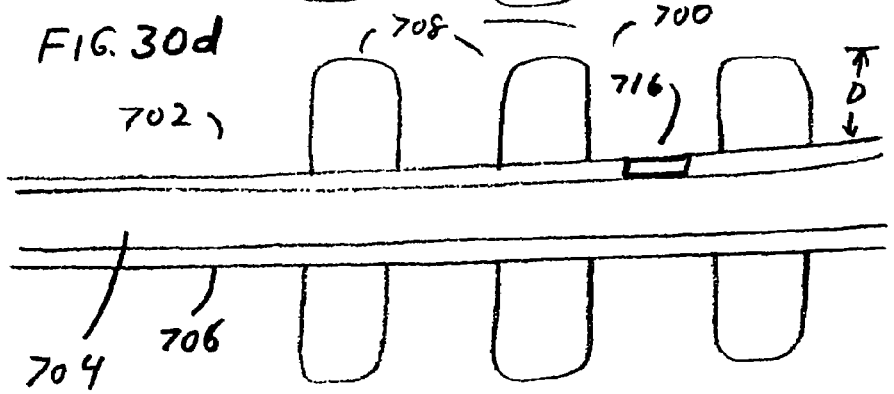

FIG. 30a through FIG. 30d illustrate exemplary embodiments of catheters of the present invention that include sensors. FIG. 30a illustrates a catheter 700 having a catheter body 702, an internal longitudinal passage 704 and a catheter wall 706. At least one distancing member 708 is positioned about the catheter body 702 for establishing the minimum distance D. A sensor 710 is positioned external to the catheter wall 706. FIG. 30b illustrates the catheter 700 having a sensor 712 positioned within one of the at least one distancing member 708. FIG. 30c illustrates the catheter 700 having a sensor 714 positioned within the longitudinal passage 704. FIG. 30d illustrates the catheter 700 having a sensor 716 integrated with the catheter wall 706.

Figure 31:
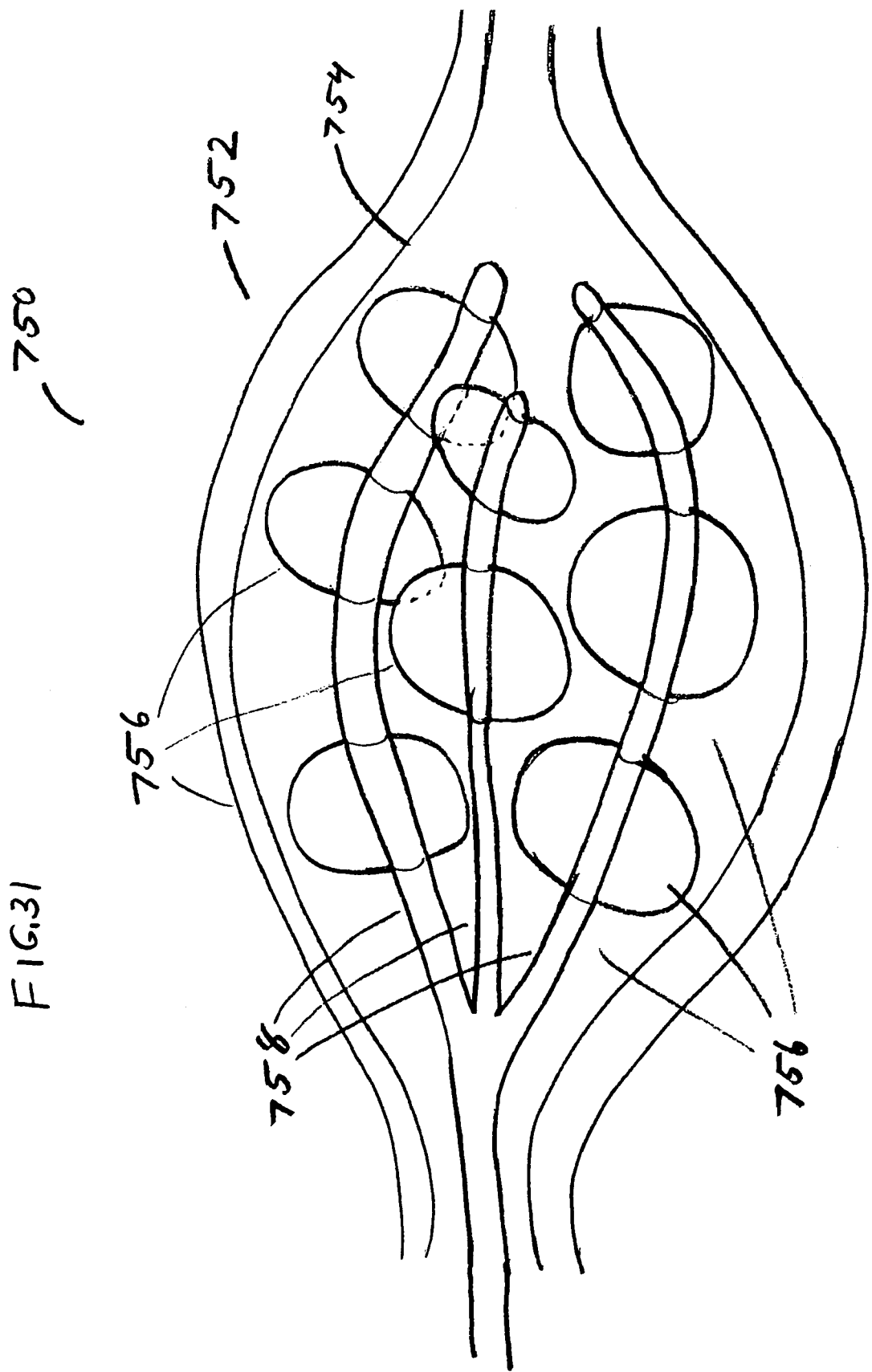
FIG. 31 illustrates an embodiment of a branched catheter of the present invention.

Embodiments of the present invention may also include a plurality of catheters or catheter sections having distancing members for deployment in a lumen. FIG. 31 illustrates an embodiment of a branched catheter 750 of the present invention, positioned in a lumen 752 having a lumen wall 754. The branched catheter 750 includes a plurality of distancing members 756 associated with a plurality of catheter branches 758. In an embodiment, the plurality of branches 758 and the plurality of distancing members 756 are adapted to provide a uniform dose of light to the lumen wall 754. In an embodiment, a branched catheter is substantially surrounded by a sheath during introduction of the catheter into a lumen, the sheath being adapted to be withdrawn from the catheter before distancing members about branches of the catheter are deployed. In an embodiment, the branches are adapted for substantially homogeneously irradiating an interior volume of a lumen when the distancing members are deployed. In an embodiment, the lumen is asymmetrical.

Figure 32:
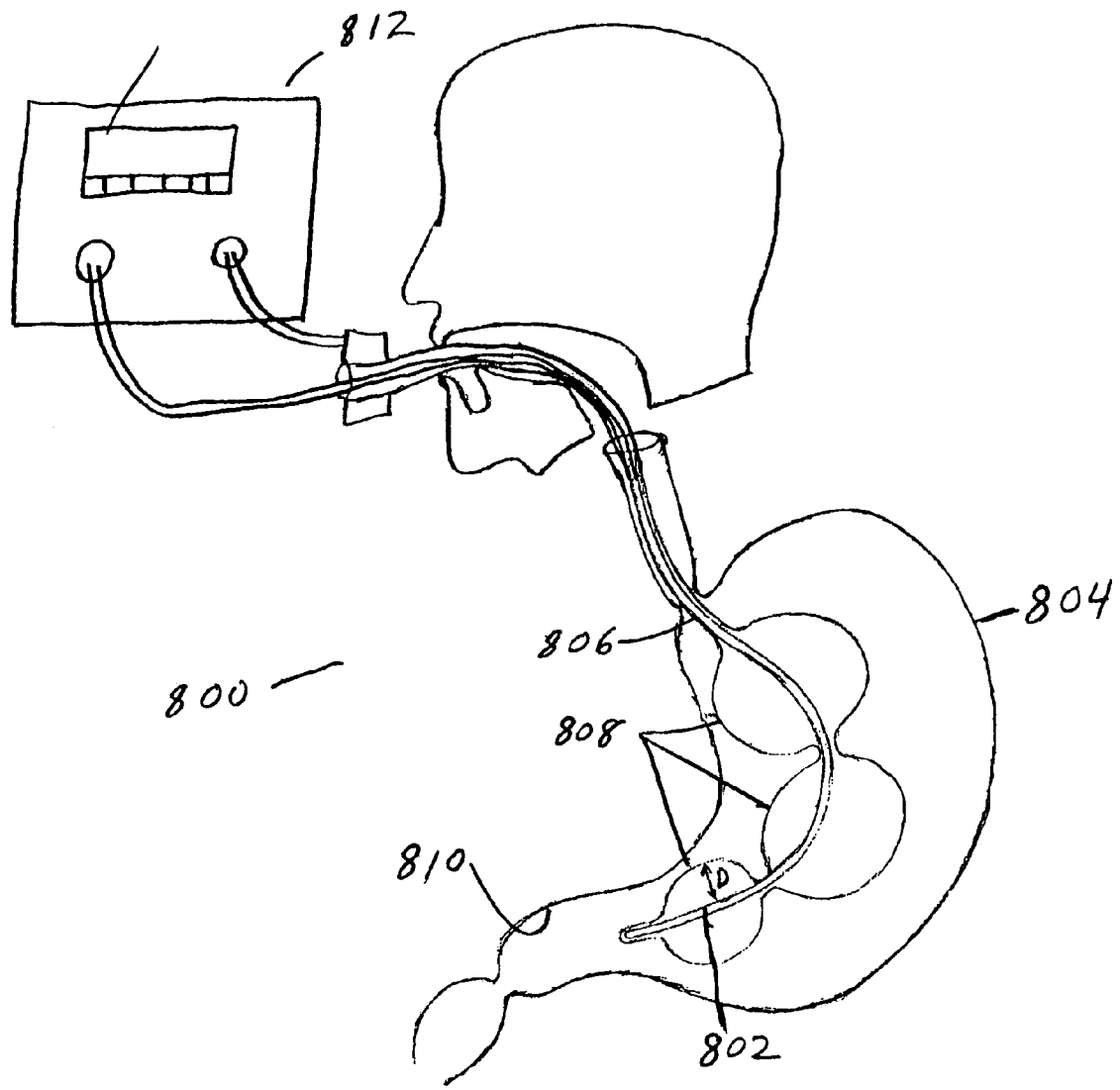
FIG. 32 illustrates an embodiment of a phototherapy system of the present invention.

FIG. 32 illustrates an embodiment of a phototherapy system 800 of the present invention. The phototherapy system 800 includes a light-emitting probe 802 for delivering light to the interior of a lumen 804 (shown as a human stomach in FIG. 32). The phototherapy system 800 also includes a catheter 806 having one or more distancing members 808 for maintaining a minimum distance D between the light-emitting probe 802 and a lumen wall 810. A control unit 812 may provide power, cooling and a user interface for the probe 802 and for the catheter 806. In an embodiment, the user interface for the catheter 806 includes controls for deployment of the one or more distancing members 808. In another embodiment, the interface for the catheter 806 also includes controls for modulating the position of the catheter 806 in the lumen 804. In one embodiment, the interface for the catheter 806 and the interface for the light-emitting probe 802 are located in the single control unit 812. In another embodiment, the interface for the catheter 806 and the interface for the light-emitting probe 802 are located in separate control units.

An exemplary embodiment of a phototherapeutic procedure according to the present invention includes the steps of: positioning a catheter that includes a light-emitting device in a lumen, insufflating the lumen, deploying one or more distancing members to establish a minimum distance between the light-emitting device and a wall of the lumen, and delivering light to the wall of the lumen. In an embodiment, the catheter and deployed distancing member are free to move within the lumen during the time that light is delivered to the lumen wall. In an embodiment, the catheter is positioned in the lumen by guiding it along a wire that has previously been positioned in the lumen using an endoscope. In another embodiment, the position of the catheter is modulated during the time that light is delivered to the wall of the lumen.

The methods and catheters of the present invention have many advantages, including but not limited to the safety and efficacy of phototherapeutic procedures in lumens. Embodiments of catheters of the present invention include distancing members that, when deployed, do not substantially distend or constrain natural movements of a lumen in which the catheter is positioned, and thereby reduce trauma to the lumen relative to the use of phototherapy catheters that distend or substantially constrain the motion of a lumen. In an embodiment, a catheter of the present invention includes a coating of lubricant. In an embodiment, the lubricant is a lubricating gel. In an embodiment, the lubricant is K-Y Jelly (a trademark of McNeil-PPC, Inc.). In an embodiment, the lubricant reduces abrasion of tissue during passage of the catheter into or out of a lumen. In an embodiment, the lubricant maintains one or more undeployed balloons in a wrapped configuration about a catheter body during insertion of the catheter into the lumen.

Embodiments of methods and catheters of the present invention can also be used effectively in irregularly shaped or asymmetric lumens. Embodiments of catheters of the present invention can be moved, modulated or dithered in position within a lumen during a phototherapy procedure, thereby enabling a substantially homogeneous dose of therapeutic light to be delivered to a wall of an irregularly shaped lumen or a lumen having portions that are difficult to otherwise access phototherapy, such as the fundus of the stomach.

Embodiments of methods and catheters of the present invention have particular advantage in phototherapy procedures for treating infections of lumens, for example, the phototherapeutic treatment of *Helicobacter pylori* (*H. Pylori*) infection of the human gut. Many photodynamic therapy methods include pretreatment of the patient with an exogenous photosensitizer to sensitize diseased tissue to light. The sensitized diseased tissue is then exposed to therapeutic light, while the simultaneous exposure of healthy tissue to the light is restricted to avoid damage to that tissue. In the case of phototherapeutic treatment of *H. Pylori* infection, the therapeutic light is absorbed primarily by an endogenous photosensitizer of the *H. Pylori* organism, leaving adjacent healthy tissue substantially undamaged during substantially homogeneous dosing of the lumen with therapeutic light.

Yet another advantage of the present invention is that embodiments of phototherapy procedures according to the present invention may be performed without visualization of the interior of a lumen during irradiation with phototherapeutic light. In an embodiment, one or more distancing members maintain one or more light-emitting devices at least a minimum distance from a lumen wall to ensure that light at the lumen wall does not exceed a desired maximum intensity without visualization.

Many changes in the details, materials, and arrangement of parts, herein described and illustrated, can be made by those skilled in the art. Although the invention has been shown and described with respect to detailed embodiments thereof, it will be understood that changes may be made without departing from the spirit and scope of the claimed invention. Accordingly, the following claims are not to be limited to the embodiments disclosed herein.

What is claimed is:

1. A method for delivering radiation into a cavity, the method comprising:
   a) positioning a catheter in the cavity, the catheter including a radiation source, an insufflation device, and at least one distancing member, the cavity having an interior surface;
   b) insufflating the cavity using the insufflation device;
   c) deploying the at least one distancing member, the at least one distancing member being adapted to provide a minimum distance between the radiation source and the interior surface of the cavity while allowing movement of the catheter within the cavity; wherein the at least one distancing member includes at least one segmented arm, the at least one segmented arm including at least two segments, the at least two segments connected by a flexible hinge, and deploying the distancing member comprises flexing the flexible hinge; and
   d) delivering radiation to the interior surface of the cavity using the radiation source.

2. The method of claim 1, wherein the at least one distancing member includes at least one balloon, and deploying the distancing member comprises expanding the balloon.

3. The method of claim 1, wherein the at least one distancing member includes at least one flexible member, and deploying the at least one distancing member comprises mechanically flexing the at least one flexible member.

4. The method of claim 3, wherein the flexible member is flexed by inflating a balloon.

5. The method of claim 1, wherein at least a portion of the at least one distancing member is substantially transparent to light.

6. The method of claim 1, wherein at least a portion of the at least one distancing member is adapted to scatter light.

7. The method of claim 1, wherein the radiation source comprises a light-emitting diode.

8. The method of claim 1, wherein the radiation source comprises an optical fiber optically coupled to a radiation source located outside the cavity.

9. The method of claim 1, wherein the movement of the catheter within the cavity is in response to natural movement of the cavity.

10. The method of claim 1, wherein the movement of the catheter within the cavity is actively controlled from outside the cavity.

11. The method of claim 1, wherein the cavity is a lumen.

12. The method of claim 11, wherein the radiation kills at least a portion of an infection in the lumen.

13. The method of claim 12, wherein the infection is a *Helicobacter pylori* infection.

14. The method of claim 1, wherein the deploying the at least one distancing member is variably controlled to achieve different minimum distances.

15. The method of claim 1, wherein the method is used to perform a diagnostic procedure.

* * * * *